(12) United States Patent
Miyazono et al.

(10) Patent No.: US 10,518,506 B2
(45) Date of Patent: Dec. 31, 2019

(54) LAYERED PRODUCT AND PROCESS FOR PRODUCING SAME

(71) Applicant: TORAY INDUSTRIES, INC., Tokyo (JP)

(72) Inventors: Koki Miyazono, Otsu (JP); Yutaka Katayama, Otsu (JP); Yusuke Kawabata, Otsu (JP); Eiichiro Tamaki, Otsu (JP); Yasuo Kubota, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 282 days.

(21) Appl. No.: 15/317,588

(22) PCT Filed: Jun. 8, 2015

(86) PCT No.: PCT/JP2015/066464
§ 371 (c)(1),
(2) Date: Dec. 9, 2016

(87) PCT Pub. No.: WO2015/190432
PCT Pub. Date: Dec. 17, 2015

(65) Prior Publication Data
US 2017/0106626 A1 Apr. 20, 2017

(30) Foreign Application Priority Data

Jun. 12, 2014 (JP) ................. 2014-121346

(51) Int. Cl.
| | | |
|---|---|---|
| *B32B 9/00* | (2006.01) | |
| *B32B 7/12* | (2006.01) | |
| *B32B 5/16* | (2006.01) | |
| *B32B 27/06* | (2006.01) | |

(Continued)

(52) U.S. Cl.
CPC ............. *B32B 9/007* (2013.01); *B32B 5/16* (2013.01); *B32B 7/12* (2013.01); *B32B 9/045* (2013.01);

(Continued)

(58) Field of Classification Search
CPC ....... B32B 9/007; G01N 27/308; H01L 29/43; H01B 1/04
See application file for complete search history.

(56) References Cited

U.S. PATENT DOCUMENTS

2011/0143101 A1 6/2011 Sandhu
2012/0301707 A1 11/2012 Kinloch et al.
(Continued)

FOREIGN PATENT DOCUMENTS

CN 102275858 A 12/2011
CN 103538312 A 1/2014
(Continued)

OTHER PUBLICATIONS

First Office Action dated Jan. 10, 2018, in Chinese Patent Application No. 201580031426.6, with English translation.
(Continued)

*Primary Examiner* — Ramsey Zacharia
(74) *Attorney, Agent, or Firm* — Birch, Stewart, Kolasch & Birch, LLP

(57) ABSTRACT

Provided are a laminate that has high smoothness, planar homogeneity, and substrate adhesion and undergoes little change in physical properties even if degradation of surface quality due to physical contact in use has occurred, and a method for producing the homogeneous laminate in a convenient manner in a small number of steps. A laminate includes a substrate made of a polymer material and a partially oxidized thin layer graphite piece layer including partially oxidized thin layer graphite pieces and having an average thickness to of 3.0 nm to 10,000 nm, the layer being formed on the substrate and bonded to the substrate via a chemical bond.

12 Claims, 1 Drawing Sheet

(51) Int. Cl.
  *H01B 1/04* (2006.01)
  *C08J 7/06* (2006.01)
  *G01N 27/30* (2006.01)
  *B32B 9/04* (2006.01)
  *B32B 27/14* (2006.01)
  *B32B 27/36* (2006.01)
  *F28F 21/02* (2006.01)

(52) U.S. Cl.
  CPC .............. *B32B 27/06* (2013.01); *B32B 27/14* (2013.01); *B32B 27/36* (2013.01); *C08J 7/06* (2013.01); *G01N 27/30* (2013.01); *G01N 27/308* (2013.01); *H01B 1/04* (2013.01); *B32B 2255/10* (2013.01); *B32B 2255/26* (2013.01); *B32B 2264/108* (2013.01); *B32B 2307/202* (2013.01); *B32B 2307/302* (2013.01); *B32B 2307/7242* (2013.01); *B32B 2439/00* (2013.01); *B32B 2439/40* (2013.01); *B32B 2457/00* (2013.01); *B32B 2509/00* (2013.01); *F28F 21/02* (2013.01)

(56) References Cited

U.S. PATENT DOCUMENTS

2013/0164612 A1  6/2013  Tanemura et al.
2013/0190449 A1  7/2013  Kinloch et al.
2013/0330477 A1  12/2013  Blair
2014/0370246 A1* 12/2014  Hurt .................. B05D 5/00
                                               428/189

FOREIGN PATENT DOCUMENTS

| JP | 2011-121828 A | 6/2011 | |
| JP | 2013-517200 A | 5/2013 | |
| JP | 2013-149604 A | 8/2013 | |
| JP | 2013-544740 A | 12/2013 | |
| JP | 2014-501681 A | 1/2014 | |
| WO | WO-2015094005 A1 * | 6/2015 | ........ H01L 21/02118 |

OTHER PUBLICATIONS

English translation of the Written Opinion of the International Searching Authority for PCT/JP2015/066464 (PCT/ISA/237) dated Nov. 2, 2016.

International Search Report for PCT/JP2015/066464 (PCT/ISA/210) dated Aug. 25, 2015.

Written Opinion of the International Searching Authority for PCT/JP2015/066464 (PCT/ISA/237) dated Aug. 25, 2015.

Japanese Office Action for Japanese Application No. 2015-529362, dated Jun. 18, 2019, with English translation.

* cited by examiner

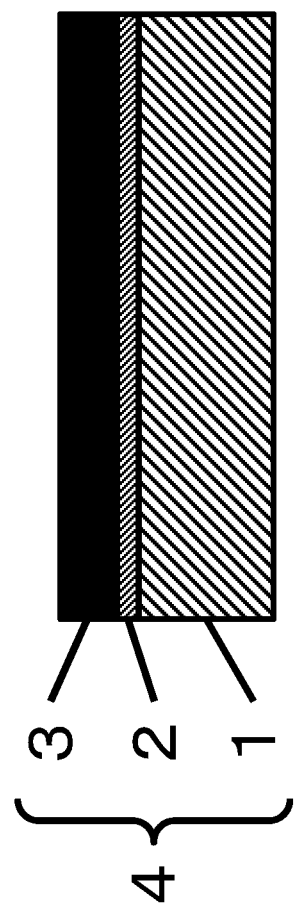

LAYERED PRODUCT AND PROCESS FOR PRODUCING SAME

TECHNICAL FIELD

The present invention relates to a laminate and a method for producing the laminate. More particularly, the invention relates to a laminate including partially oxidized thin layer graphite pieces; an electrode material, a heat sink material, and a gas barrier material, each including the laminate; and a method for producing the laminate in a convenient manner in a small number of steps.

BACKGROUND ART

Graphite, which has long been known as a carbon material having many excellent properties, such as high electrical conductivity, heat resistance, lightness, low thermal expansivity, high thermal conductivity, and self-lubricating properties, has been used in many applications. In addition, new carbonaceous materials similar to graphite, such as graphite sheets obtained by carbonizing resin materials by burning and nano-carbon materials including fullerene and carbon nanotubes, have recently been discovered to have many excellent properties that graphite also has and increasingly used in wide variety of applications. More recently, methods for producing graphene, which constitutes part of graphite and has a thickness on the order of nanometers and a structure in which numbers of benzene ring structures are two-dimensionally arranged in an adjacent manner, and thin layer graphite, which is formed of multi-layer graphene, have been discovered, and research and development has actively been conducted to use these new materials.

Graphene and thin layer graphite have many excellent physical properties, such as high strength, high elasticity, high mobility, high gas barrier properties, and good light transmission due to being thin, as well as high electrical conductivity and high thermal conductivity, which graphite also has, and are also chemically stable. Thus, their applicability wider than that of graphite has been studied. Methods for producing graphene and thin layer graphite are roughly classified into three methods, specifically as follows:

i) A gas phase method, in which a very thin graphene of a single layer or a few layers is formed by chemical vapor deposition (CVD).
ii) A solid phase method, in which a polymer film that is readily carbonized, such as polyimide, is burnt to obtain a carbonized sheet having a thickness of a dozen or more micrometers.
iii) A liquid phase method, in which granular natural graphite or artificial graphite is chemically treated to obtain thin-layered pieces.

Of these, the liquid phase method can provide a great amount of graphene or thin layer graphite pieces relatively in a short time. The liquid phase method can relatively easily control the amount of addition of oxygen-containing functional groups (i.e., the degree of oxidation) during processes including a reduction process, thereby producing partially oxidized thin layer graphite pieces having a desired degree of oxidation, and thus has been receiving attention. The graphene or thin layer graphite obtained by this method is in the form of pieces. Being difficult to use as it is, the graphene or thin layer graphite is handled in the form of a dispersion of pieces and used in various applications. For example, a layered film made of pieces from a dispersion laminated on top of each other is variously used. Uses in the following several applications are expected.

Conventionally, in the fields of semiconductors and electronics, electric wiring elements made mainly of rare metals have been previously developed, and large numbers of excellent products have been marketed. Rare metals, however, are expensive for their limited availability, and it is desired to reduce the amount used for electrodes and circuit materials as much as possible. In addition, heat generation accompanied by more compact wiring arrangements and many other problems have recently been becoming evident. As an alternative to such metals, or as a material that dissipates heat generated, carbon materials are particularly expected to be used. The production of elements and devices from carbon materials by nanotechnology has found to have the potential to provide apparatuses produced from the metal with new functionalities, such as flexibility, lightness, improved mechanical strength, and a reinforced structure, and achieve material replacement associated therewith. Furthermore, carbon materials, for their properties metals do not have, such as sliding properties and biocompatibility, have been increasingly used in a wide variety of applications.

Continuing the description, in the field of household electronic appliances, the recent further miniaturization of computers focusing on improved performance and portability has encouraged the widespread use of information terminal devices, such as tablet computers, cellular phones, and smartphones. Nevertheless, rare metals have gradually been becoming difficult to obtain. For the problem of heat generation, which has been becoming evident, it is desired to develop readily available electrically conductive materials and thin and efficient heat sink materials that can be used in small devices. These materials are used also for solid films and circuits having electrical conductivity at some parts and insulation properties at other parts. The information terminal devices have display units having excellent display functions, and the units are made of materials sensitive to moisture and oxygen. To provide long-term durability, there is a need for materials having gas barrier properties against oxygen and water vapor. For the gas barrier properties, there is a need also in high-pressure gas (e.g., natural gas, hydrogen gas, and other gases) tanks used in natural gas vehicles, fuel cell vehicles, and other vehicles, which are very effective in settling environmental issues; gas supply hoses; flexible pipes in hydrogen gas stations; and other applications.

Regarding portability, numbers of highly accurate portable sensor devices have been developed with which anyone can check the surrounding environment and his or her condition anytime anywhere. Portable sensor devices are broadly classified into physical sensors and chemical sensors that can detect ions, molecules, such as enzymes and DNA, gases, and other substances. The latter chemical sensors are capable of recognizing target substances such as ions and molecules and converting and amplifying signals. In particular, in signal conversion, which is the heart of chemical sensors, an electrode in the form of a flat film connected to a transducer that amplifies signals receives ions and molecules. Signals include light signals, such as fluorescence; signals from measurements of mass changes and thermal outputs; and electrical signals, such as membrane potential and oxidation-reduction current. These signals are received based on the mode of each signal, and measurement results are output. In particular, an electrode material portion that serves to convey electrical signals between the film portion and the transducer is incorporated, for ease of measurement, into a card or chip in which a sample contact portion and the electrode material portion are integrated. The electrode material portion is used once or several times at most and disposed of without being reused. Since the electrode material portion is used once or several times at most, several spare elements for subsequent use are typically provided at hand. In selecting an electrode material, there is preferably no need to consider how long, by whom, and where the element is used. For this reason, the element needs to produce a constant stable performance over a long period of time, allow stable measurement even after being attached to and detached from a measuring apparatus for several times, and be inexpensive and readily available. Thus, there is a need to develop elements having a sample contact portion and an electrode material portion less prone to reduction in performance after long-term storage and use.

A description will now be given of the related art from the viewpoint of electrical conductivity, heat sink properties, and gas barrier properties.

There has been disclosed a technique for forming an electrically conductive layer from a paste made of a carbon material and a binder, which electrically conductive layer is used as an electrode element of an electrochemical sensor (see Patent Documents 1 and 2). In this technique, an electrically conductive material, such as carbon black, and a binder made mainly of a resin are mixed and dispersed to prepare a paste, and the paste is applied to a substrate by screen printing or other methods to form an electrically conductive layer, which is used as an element. This technique can form a good electrically conductive layer but, on the other hand, from the viewpoint of the application of carbon black, requires a large amount of binder in preparing a paste so that the paste is unbreakable. Such a large amount of binder tends to reduce the contact frequency between carbon black particles, resulting in an electrically conductive layer with low electrical conductivity. Furthermore, the electrically conductive layer and the substrate are poorly bonded and readily separated, and thus there is a need to use a special material less smooth and difficult to handle. Despite the use of such a special material, the electrically conductive layer is readily peeled off, has low and variable electrical conductivity, and is poor in handleability and quality stability.

There has been disclosed a technique for applying a dispersion of carbon material pieces to form an electrode for electrochemical measurements (see Patent Document 3). In this technique, a dilute homogeneous aqueous dispersion of graphene oxide prepared mainly by a chemical method is thinly applied to a metal layer used as an electrically conductive layer, not across electrodes made of the metal layer, and a pattern is formed. By the action of the graphene oxide to facilitate the transportation of redox species to the surface, higher sensitivities in electrochemical measurements are achieved. The graphene and the metal layer are weakly adsorbed to each other via the hydrophobic interaction between a thiol compound covalently bonded to the metal layer and the graphene. However, depending on the stronger action in a measurement environment, for example, the change in temperature and the change in the amount of acid/alkaline, the adsorption between the graphene and the metal layer is difficult to maintain, and the graphene is readily peeled off. This results in an element with low long-term stability, and the element can be used in very limited conditions. In addition, the element tends to indicate variable values upon abrasion or even slight peeling and thus is difficult to handle.

Furthermore, there has been disclosed a technique for fine processing of an electronic device using thin graphene flakes (see Patent Document 4). This is a basic technique for patterning a very thin graphene layer utilizing the affinity between a specific portion of a substrate hydrophilized in advance and graphene. The technique, which is intended for use for semiconductor materials and transparent electrodes, can theoretically be applied only to thicknesses of graphene of one layer or two to three layers.

Regarding the heat sink material described above, there has been disclosed a technique for a heat radiating plate produced by rolling graphite into a thin plate (see Patent Document 5). In this technique, expanded graphite obtained by heat expansion is rolled into a thin plate, and then aluminum foil is tightly laminated all over via an adhesive layer to form a heat radiating plate, thereby obtaining a light and bendable material. However, since graphite is rolled, there is a limit as to how thin the heat sink can be, and, in addition, the heat radiating plate has poor conformability to fine shapes because of the metal exterior. Furthermore, the aluminum foil and the thin-plate graphite layer are intervened by the adhesive layer having low affinity, and therefore the adhesion is still poor.

Regarding the gas barrier material described above, there has been disclosed a technique for a composite sheet containing flake graphite (see Patent Document 6). In this technique, the composite sheet is made of flake graphite and layered silicate irregularly superposed on each other, and thus the sheet itself can be used as a self-supported film. However, the interaction between the thin-layered graphite and the layered silicate is weak, and the composite sheet has low resistance to long-time water vapor exposure. Furthermore, when a synthetic resin is used as a support, and the composite sheet is formed thereon, the sheet may readily be peeled off because of the low adhesion to the synthetic resin.

PRIOR ART DOCUMENTS

Patent Documents

Patent Document 1: JP 2006-308463 A
Patent Document 2: JP 2013-170957 A
Patent Document 3: JP 2012-181085 A
Patent Document 4: JP 2011-121828 A
Patent Document 5: JP 2005-252190 A
Patent Document 6: JP 2011-195408 A

SUMMARY OF THE INVENTION

Problems to be Solved by the Invention

An object of the present invention is to provide a thin material made of a laminate of thin layer graphite pieces having high substrate adhesion.

Means for Solving the Problems

To solve the problems described above, the present invention has the following structure:
(1) A laminate comprising:
a substrate made of a polymer material; and
a partially oxidized thin layer graphite piece layer comprising partially oxidized thin layer graphite pieces and having an average thickness to of 3.0 nm to 10,000 nm,
the layer being formed on the substrate and bonded to the substrate via a chemical bond.

Preferred aspects of the laminate include the following:

(2) The laminate according to the foregoing, wherein the partially oxidized thin layer graphite pieces have a degree of oxidation (O/C) of 0.07 to 0.85.

(3) The laminate according to any of the foregoing, wherein the partially oxidized thin layer graphite piece layer is substantially free of a binder.

(4) The laminate according to any of the foregoing, wherein the chemical bond is selected from the group consisting of an ionic bond, a hydrogen bond, and a covalent bond.

(5) The laminate according to any of the foregoing, further comprising a binding agent having a first chemical bond with the substrate and a second chemical bond with the partially oxidized thin layer graphite pieces, through which binding agent the bond via a chemical bond is formed.

(6) The laminate according to the foregoing, wherein the binding agent has a basic functional group and a functional group selected from the group consisting of a hydroxyl group, an amino group, an ammonium group, a carboxyl group, and an alkoxysilyl group.

(7) The laminate according to any of the foregoing, wherein the binding agent is a polymer binding agent.

(8) The laminate according to any of the foregoing, wherein the partially oxidized thin layer graphite piece layer has a surface resistivity Ra with a coefficient of variation CV of 10% or less.

(9) The laminate according to any of the foregoing, wherein the partially oxidized thin layer graphite piece layer has an insulating portion having a degree of oxidation (O/C) of at least 0.15 and an electrically conductive portion having a degree of oxidation (O/C) of less than 0.15.

The present invention provides the following articles comprising the laminate according to any of the foregoing.

(10) An electrode material comprising the laminate according to any of the foregoing.

(11) A heat sink material comprising the laminate according to any of the foregoing.

(12) A gas barrier material comprising the laminate according to any of the foregoing.

(13) A gas tank comprising the gas barrier material according to the foregoing.

The present invention provides the following method for producing a laminate.

(14) A method for producing a laminate, the method comprising in sequence:

loading a binding agent onto a substrate made of a polymer material, the binding agent having a first binding functional group capable of forming a chemical bond with the substrate and a second binding functional group capable of forming a chemical bond with partially oxidized thin layer graphite pieces, thereby chemically binding the substrate to the first binding functional group;

loading a coating agent comprising partially oxidized thin layer graphite pieces onto the binding agent by application, thereby chemically binding the second binding functional group to the partially oxidized thin layer graphite pieces; and reducing at least some of the partially oxidized thin layer graphite pieces in a liquid.

The present invention also provides the following easy-adhesion film.

(15) An easy-adhesion film for partially oxidized graphite, the film comprising;

a substrate made of a polymer material; and a binding agent on the substrate, the agent having a basic functional group and a functional group selected from the group consisting of a hydroxyl group, an amino group, an ammonium group, a carboxyl group, and an alkoxysilyl group.

Effects of the Invention

The laminate of the present invention has a laminated structure in which partially oxidized thin layer graphite pieces and a substrate tightly adhere to each other. Thus, the laminate has high electrical conductivity and undergoes little change in electrically conductive properties even if degradation of surface quality, such as peeling and wear, has occurred due to physical contact in use, such as being rubbed and hit. The laminate also has excellent gas barrier properties.

BRIEF DESCRIPTION OF THE DRAWING

FIG. 1 is a schematic cross-sectional view of a laminate according to of the present invention.

MODE FOR CARRYING OUT THE INVENTION

As shown in FIG. 1, a laminate (4) of the present invention has a substrate (1) made of a polymer material and a layer (3) comprising partially oxidized thin layer graphite pieces (hereinafter the partially oxidized thin layer graphite is also referred to as a "thin layer graphite" for short, and the layer comprising partially oxidized thin layer graphite pieces is also referred to as a "partially oxidized thin layer graphite piece layer" or a "thin layer graphite piece layer" for short). The substrate and the partially oxidized thin layer graphite piece layer have a structure in which the substrate and the partially oxidized thin layer graphite piece layer on the substrate are bonded to each other via a chemical bond.

The substrate made of a polymer material will be described. The substrate in the present invention may depend on the properties required for an application in which the laminate of the present invention is used. Any material that can support the partially oxidized thin layer graphite piece layer on the substrate may be used, and polymer materials are used. Polymer materials are used because they have high strength and rigidity described below and thus can successfully pass processes such as taking up with a roller, and because they can successfully form a chemical bond with a binding agent described below. In particular, polymer materials are preferred because they are flexible and light and readily form a strong chemical bond with a binding agent described below or directly with partially oxidized thin layer graphite pieces.

Specific examples of the polymer material in the present invention include polyester polymers, polyamide polymers, polyimide polymers, vinyl polymers such as polyolefin polymers, which can be synthesized by vinyl addition polymerization, fluorine polymers, polycarbonate polymers, polyether polymers, polyphenylene sulfide polymers, polyether ether ketone polymers, polyether ketone ketone polymers, cellulose polymers, aromatic or aliphatic ketone polymers, elastomers such as natural rubber and synthetic rubber, epoxy resins, and other engineering plastics.

Of these polymer materials, specifically, vinyl polymers are preferred, and examples include polyethylene, polypropylene, polybutylene, polymethylpentene, polystyrene, polyacrylic acid, polymethacrylic acid, polymethyl methacrylate, polyacrylonitrile, polytetrafluoroethylene, polyvinylidene fluoride, polyvinylidene chloride, polyvinylidene cyanide, polyvinyl alcohol, and polyvinylpyrrolidone. These may be polymers obtained by polymerization of a single monomer or copolymers obtained by polymerization of a plurality of monomers. Among vinyl polymers, ethylene-vinyl alcohol copolymers are suitable for use for a substrate of a gas barrier material described below.

Other preferred polymer materials are polyamide polymers. Specific examples include polycaproamide (polyamide 6), polyhexamethylene adipamide (polyamide 6,6), polypentamethylene adipamide (polyamide 5,6), polytetramethylene adipamide (polyamide 4,6), polytetramethylene sebacamide (polyamide 4,10), polyhexamethylene sebacamide (polyamide 6,10), polypentamethylene sebacamide (polyamide 5,10), polyhexamethylene dodecamide (polyamide 6,12), polyundecaneamide (polyamide 11), polydodecaneamide (polyamide 12), polydecamethylene terephthalamide (polyamide 10T), polycaproamide/polyhexamethylene terephthalamide copolymer (polyamide 6/6T), polyhexamethylene adipamide/polyhexamethylene terephthalamide copolymer (polyamide 6,6/6T), polyhexamethylene adipamide/polyhexamethylene isophthalamide copolymer (polyamide 6,6/6I), polyhexamethylene adipamide/polyhexamethylene isophthalamide/polycaproamide copolymer (polyamide 6,6/6I/6), polyhexamethylene terephthalamide/polyhexamethylene isophthalamide copolymer (polyamide 6T/6I), polyhexamethylene terephthalamide/polydodecaneamide copolymer (polyamide 6T/12), polyhexamethylene adipamide/polyhexamethylene terephthalamide/polyhexamethylene isophthalamide copolymer (polyamide 6,6/6T/6I), polyxylylene adipamide (polyamide XD6), polyhexamethylene terephthalamide/poly-2-methylpentamethylene terephthalamide copolymer (polyamide 6T/M5T), polyhexamethylene terephthalamide/polypentamethylene terephthalamide copolymer (polyamide 6T/5T), and aromatic polyamides (including meta and para forms). In addition, polyamide polymers of other aromatic, aliphatic, or alicyclic dicarboxylic acids and other aromatic, aliphatic, or alicyclic diamine components or polyamide polymers of an aminocarboxylic acid compound alone, which is a single aromatic, aliphatic, or alicyclic compound having both a carboxylic acid and an amino group, may be used. These polyamide polymers may be used in a combination of two or more.

Still other preferred polymer materials are polyester polymers. Specific examples include polyethylene terephthalate, polypropylene terephthalate (also referred to as polytrimethylene terephthalate), polybutylene terephthalate (also referred to as polytetramethylene terephthalate), polyethylene naphthalate, polycyclohexanedimethanol terephthalate, which are formed from a dicarboxylic acid and a diol, and liquid crystal polyesters composed mainly of an aromatic hydroxycarboxylic acid and having thermotropic liquid crystallinity. Other examples of polyester polymers include homopolyesters of a hydroxycarboxylic acid monomer, and examples of preferred poly(hydroxycarboxylic acids) include polylactic acid, poly(3-hydroxypropionate), poly(3-hydroxybutyrate), and poly(3-hydroxybutyrate valerate). These polyester polymers may be copolymerized with other components without departing from the spirit of the present invention, and examples of dicarboxylic acid compounds include aromatic, aliphatic, and alicyclic dicarboxylic acids, such as terephthalic acid, isophthalic acid, naphthalenedicarboxylic acid, diphenyldicarboxylic acid, anthracenedicarboxylic acid, phenanthrenedicarboxylic acid, diphenyl ether dicarboxylic acid, diphenoxyethanedicarboxylic acid, diphenylethanedicarboxylic acid, adipic acid, sebacic acid, 1,4-cyclohexanedicarboxylic acid, 5-sodium sulfoisophthalic acid, 5-tetrabutylphosphonium isophthalic acid, azelaic acid, dodecanedioic acid, and hexahydroterephthalic acid. Furthermore, derivatives thereof substituted, for example, with an alkyl group, an alkoxy group, an allyl group, an aryl group, an amino group, an imino group, or a halide may be used. Adducts, structural isomers, and optical isomers thereof may also be used. Examples of diol compounds include aromatic, aliphatic, and alicyclic diol compounds, such as ethylene glycol, propylene glycol, butylene glycol, pentanediol, hexanediol, 1,4-cyclohexanedimethanol, neopentyl glycol, hydroquinone, resorcin, dihydroxybiphenyl, naphthalenediol, anthracenediol, phenanthrenediol, 2,2-bis(4-hydroxyphenyl)propane, 4,4'-dihydroxydiphenyl ether, and bisphenol S. Furthermore, derivatives thereof substituted, for example, with an alkyl group, an alkoxy group, an allyl group, an aryl group, an amino group, an imino group, or a halide may be used. In addition, structural isomers and optical isomers thereof may be used. These dicarboxylic acid compounds and diol compounds to be copolymerized may be used alone or in a combination of two or more without departing from the spirit of the invention.

Of these polymer materials, polyester polymers, polyamide polymers, vinyl polymers, and polyimide polymers, which have high heat resistance and formability, are preferred for the substrate of the laminate of the present invention. In view of the use for a substrate of an electrode material or a heat sink material described below, polyester polymers, polyamide polymers, and polyimide polymers having a melting point of 150° C. or higher are more preferred. The electrode material or the heat sink material described below is required to show a stable performance with little change due to humidity in physical properties of the substrate, and thus polyester polymers and polyimide polymers having a melting point of 200° C. or higher are particularly preferred. In the case of a gas barrier material described below, it is preferred that a substrate itself have high gas barrier properties, and thus vinyl polymers (ethylene-vinyl alcohol copolymers) and polyamide polymers are particularly preferred for the substrate. Specific examples of particularly preferred polyamide polymers include polycaproamide (polyamide 6), polyhexamethylene adipamide (polyamide 6,6), polypentamethylene adipamide (polyamide 5,6), polyhexamethylene sebacamide (polyamide 6,10), polypentamethylene sebacamide (polyamide 5,10), polytetramethylene sebacamide (polyamide 4,10), polyundecaneamide (polyamide 11), and polydodecaneamide (polyamide 12). Combining a substrate made of such a polyamide polymer with the partially oxidized thin layer graphite piece layer of the present invention can provide high oxygen gas barrier properties and high hydrogen gas barrier properties. "Melting point" as used herein refers to a peak temperature determined by the method described in Section G in Examples below.

To the polymer material used for the substrate of the present invention, rubbers may optionally be added in order to provide toughness at low temperatures, to the extent that the properties of the polymer material are not adversely affected. Examples of preferred rubbers include diene rubbers, such as polybutadiene, polyisoprene, styrene-butadiene random copolymers, block copolymers, and hydrogenated block copolymers, acrylonitrile-butadiene copolymers, and butadiene-isoprene copolymers; ethylene-propylene random copolymers and block copolymers; ethylene-butene random copolymers and block copolymers; copolymers of ethylene and α-olefins; ethylene-unsaturated carboxylic acid (e.g., ethylene-acrylic acid, ethylene-methacrylic acid) copolymers; ethylene-unsaturated carboxylic ester (e.g., ethylene-acrylic acid ester, ethylene-methacrylic acid ester) copolymers; ethylene-unsaturated carboxylic acid-unsaturated carboxylic acid metal salt (e.g., ethylene-acrylic acid-acrylic acid metal salt, ethylene-methacrylic acid-methacrylic acid metal salt) copolymers in which some of the unsaturated carboxylic acids are substituted with metal ions; acrylic elastomeric polymers, such as acrylic acid ester-butadiene copolymer and butyl acrylate-butadiene copolymer; ethylene-fatty acid vinyl (e.g., ethylene-vinyl acetate) copolymers; ethylene-propylene-unconjugated diene ternary copolymers, such as ethylene-propylene-ethylidenenorbornene copolymer and ethylene-propylene-hexadiene copolymer; butylene-isoprene copolymer; chlorinated polyethylene; and modified compounds thereof. Two or more of these rubbers may be added. When the laminate of the present invention is used as an oxygen gas barrier material or a hydrogen gas barrier material described below and the material is used particularly for a gas tank or a gas supply hose, high toughness at low temperatures is desired, and thus it is preferable to add the above-described rubbers to the polymer material used for the substrate of the present invention.

Although the substrate in the present invention may be a fiber substrate such as a woven fabric, a knitted fabric, or a nonwoven fabric, the substrate is preferably in the form of a sheet to precisely form the above-described partially oxidized thin layer graphite piece layer. The sheet form is a particularly preferred form for an electrode material and a heat sink material described below. When used as a gas barrier material described below, the substrate can be in various forms depending on the intended use, such as a sheet with a thickness of approximately 1 mm to 10 mm, a film with a thickness of approximately 0.1 µm to 1,000 µm, a hose, a tube, and a molded article with a thickness of 1 cm or more. When used for a high-pressure gas tank, the substrate is preferably in the form of a cylinder with at least one end sealed. A resin in the form of a cylinder that confines gas at the innermost of a gas tank is referred to as an inner liner resin. When a thin layer graphite piece layer is formed on the inner liner resin by outer and/or inner coating, the inner liner resin and the thin layer graphite piece layer tightly adhere to each other with the inner liner resin and thin layer graphite pieces in direct contact or via a binding agent loaded onto the inner liner resin serving as the substrate, as described below.

The substrate in the present invention preferably has an average thickness tb of 1.0 µm to 10 cm. Specifically, the average thickness tb of the laminate of the present invention depends on the intended use. When the laminate is used as an electrode material, stable maintenance of the thin layer graphite piece layer formed on the substrate needs to be taken into account. Particularly when an electric current is passed through the thin layer graphite piece layer of the present invention, the substrate needs to exhibit sufficient insulation properties. From this standpoint, the average thickness tb of the substrate is preferably 1.0 µm to 1,000 µm. When the laminate is used as an electrode material, the average thickness tb of the substrate is more preferably 5.0 µm to 500 µm in terms of high flexibility and transportability, particularly preferably 10 µm to 300 µm in terms of high process passability and winding properties in forming an electrode material, most preferably 25 µm to 250 µm in terms of ease of stable formation into the shape of a card or a chip. When the laminate is used as a heat sink material, the heat sink material conforms to the shape of a place where it is applied, and thus the average thickness tb of the substrate is preferably 1.0 µm to 100 µm. In the case of a heat sink material, the average thickness tb of the substrate is particularly preferably 5.0 µm to 80 µm to dissipate a sufficient amount of heat. When the laminate is used as a gas barrier material, it is preferred that the substrate have a strength sufficient to serve as a support and be provided with a predetermined thickness to have gas blocking properties. In such applications, the average thickness tb of the substrate is preferably 1.0 µm to 10 cm. In the case of a gas barrier material, the average thickness tb of the substrate is more preferably 5.0 µm to 8 cm in terms of high transportability and lightness. When the substrate of the gas barrier material is tubular, tb means an average thickness of the tube wall. The average thickness tb of the substrate can be measured with a light microscope, a laser microscope, a scanning electron microscope, or by a method in Section D in Examples below using a transmission electron microscope, a thickness meter, and vernier calipers. Materials, preferred polymer materials, of such a substrate may be used alone or in a combination of two or more.

The substrate used for the laminate of the present invention binds to partially oxidized thin layer graphite pieces via a chemical bond. The chemical bond is preferably a bond selected from an ionic bond, a hydrogen bond, and a covalent bond. When a binding agent described below is used, the substrate binds to the binding agent via a first chemical bond with a first binding functional group of the binding agent. In this case, the substrate can be used as it is because it has sites that form chemical bonds, such as functional groups and electrons that can form chemical bonds. Preferably, the substrate can be used after the chemical bond formability of the substrate is increased by physically and/or chemically pretreating the substrate and then activating the functional group and the electrons that can form chemical bonds or by providing a further functional group on the surface of the substrate. Specific examples of preferred physical pretreatments include UV ozonation and atmospheric-pressure plasma treatment. According to these methods, the pretreatment can be carried out in a short time from 1 second to 15 minutes. Examples of preferred chemical pretreatments include the use of strong acids including sulfuric acids, such as concentrated sulfuric acid, fuming sulfuric acid, and dilute sulfuric acid, and nitric acids, such as concentrated nitric acid, fuming nitric acid, and dilute nitric acid, and strong bases including aqueous solutions of sodium hydroxide and potassium hydroxide. When these are used, the pretreatment can be carried out over 1 second to 24 hours optionally with heating. That is to say, the substrate used for the laminate of the present invention is preferably a physically and/or chemically pretreated substrate. The above-described polymer materials are preferably physically pretreated because functional groups tend to be formed effectively even in a short pretreatment time. The pretreatment of the polymer materials is preferred particularly because the pretreatment forms further functional groups such as hydroxyl, carboxyl, and sulfonic.

A description will now be given of the partially oxidized thin layer graphite piece layer. As used herein, "partially oxidized" in the term "partially oxidized thin layer graphite piece" means that the thin layer graphite piece has an oxygen-containing functional group, for if "wholly" oxidized, all the carbon atoms in the above-described carbon material having a graphite structure are bound to oxygen atoms to become carbon dioxide. The partially oxidized thin layer graphite piece layer may be in direct contact with the substrate or separated from the substrate by the presence of a binding agent.

The partially oxidized thin layer graphite pieces are prepared, for example, by performing a physical thin-layering process and/or a chemical thin-layering process as described below. The partially oxidized thin layer graphite pieces are in the form of flakes and have high substrate adhesion as the described below, and thus the partially oxidized thin layer graphite pieces preferably have a degree of oxidation (the number of oxygen atoms/the number of carbon atoms (O/C)) of 0.07 to 0.85. To achieve higher electrical conductivity, thermal conductivity, and gas barrier properties, the degree of oxidation is more preferably 0.08 to 0.75. Furthermore, to achieve very excellent electrical conductivity and thermal conductivity so that a desired electrode material and heat sink material described below can be formed, the degree of oxidation is particularly preferably 0.09 to 0.13. To achieve very excellent gas barrier properties so that a desired gas barrier material described below can be formed, the degree of oxidation is particularly preferably 0.10 to 0.65. The degree of oxidation (O/C) as used herein means a state in which oxygen-containing groups are added to thin layer graphite pieces by performing a physical thin-layering process and/or a chemical thin-layering process, and some of the oxygen-containing functional groups remain after an optional reduction treatment described below. The degree of oxidation is a ratio of the number of oxygen atoms in thin layer graphite pieces in such a state to the number of carbon atoms and determined by the method described in Section A in Examples below.

In the laminate of the present invention, the average thickness T of the partially oxidized thin layer graphite pieces constituting the partially oxidized thin layer graphite piece layer is preferably as small as possible so that pieces in the form of flakes can be horizontally laminated on top of each other to exhibit a high degree of flatness and smoothness and high durability. The thickness of a partially oxidized thin layer graphite piece means a size (i.e., thickness) in the direction perpendicular to the plane of a planar structure formed when the thin layer graphite piece is loaded onto a substrate plane. The average thickness T of the thin layer graphite pieces is preferably 0.3 nm to 100 nm. In any case where the thin layer graphite pieces are used to form an electrode material, a heat sink material, or a gas barrier material described below, the average thickness T is more preferably 0.6 nm to 50 nm to allow the thin layer graphite pieces to readily form and maintain a favorable laminated structure. Furthermore, to readily form, as a smooth surface, a partially oxidized thin layer graphite-containing layer formed to have good coating properties and little or no coarse grain, the average thickness T is particularly preferably 1.0 nm to 30 nm. In addition to the foregoing advantages, in terms of the economic advantage of the reduction in process cost of peeling, the average thickness T is most preferably 1.5 nm to 20 nm. The average thickness T of thin layer graphite pieces can be determined using a scanning electron microscope, a laser microscope, or a transmission electron microscope described in Section D in Examples below.

In the laminate of the present invention, the partially oxidized thin layer graphite pieces constituting the partially oxidized thin layer graphite piece layer preferably has a planar size of 0.1 μm to 200 μm. When the laminate is used as an electrode material, the size influences the degree of electrical conductivity which is expressed by lamination of pieces, and thus the average size L is preferably 0.1 μm to 100 μm, more preferably 0.5 μm to 50 μm, particularly preferably 1.0 μm to 30 μm. When the laminate is used as a heat sink material, to reduce the interfacial thermal resistance between pieces, the average size L is preferably 0.1 μm to 100 μm, more preferably 0.5 μm to 50 μm, particularly preferably 1.0 μm to 30 μm. When the laminate is used as a gas barrier material, laminated partially oxidized thin layer graphite pieces having appropriate sizes form a fine laminated structure to provide gas barrier properties, and thus the average size L is preferably 0.1 μm to 100 μm, more preferably 0.5 μm to 50 μm, particularly preferably 1.0 μm to 30 μm. The average size L of partially oxidized thin layer graphite pieces can be determined using a light microscope, an atomic force microscope, or by the observation using a laser microscope in Section E in Examples below.

The partially oxidized thin layer graphite piece layer in the present invention, when combined with the substrate to form a laminate and used as an electrode material, has high electrical conductivity. Partially oxidized thin layer graphite pieces efficiently come into contact and adhere to each other. After the partially oxidized thin layer graphite piece layer is formed, performing a reduction treatment described below provides a metallic-lustered electrode layer that is thin, smooth, and highly electrically conductive and made of reduced thin layer graphite pieces. In practice, the partially oxidized thin layer graphite pieces are not completely reduced as described below, and functional groups partially remain. Therefore, the partially oxidized thin layer graphite pieces substantially remain partially oxidized thin layer graphite pieces, though they become partially reduced thin layer graphite pieces with some of the functional groups reduced. Furthermore, patterning by reduction described below makes partially oxidized thin layer graphite and partially reduced thin layer graphite distinctively appear with different degrees of oxidation (O/C). Thus, partially oxidized thin layer graphite with some of the oxygen-containing functional groups reduced is herein referred to as partially reduced thin layer graphite. A layer containing partially reduced thin layer graphite is also referred to hereinafter as a "partially reduced thin layer graphite layer".

In this case, the surface conductivity of the electrode layer, i.e., the partially oxidized thin layer graphite piece layer, preferably, the partially reduced thin layer graphite piece layer subjected to a reduction treatment, is defined as Ra. In electrode material applications, Ra is preferably as low as possible to exhibit higher electrical conductivity. Thus, Ra is preferably 1,000 Ω/sq or lower, more preferably 500 Ω/sq or lower, particularly preferably 300 Ω/sq or lower. A decrease in Ra may result from an increase in electrode layer thickness. An increase in electrode layer thickness tends to result in peeling due to physical contact described below, promoting the degradation of surface quality due to wear. Thus, Ra is preferably at least 0.1 Ω/sq, more preferably at least 1 Ω/sq. The surface resistivity Ra can be determined by the method of Section B in Examples below.

The partially oxidized thin layer graphite piece layer of the present invention is formed on the substrate as described above and exhibits excellent electrical conductivity particularly when used as an electrode material. Furthermore, the electrical conductivity preferably does not vary depending on the place on the surface of the electrode layer of the partially oxidized thin layer graphite piece layer. For use in many applications, the electrical conductivity is preferably stable and does not vary depending on the production lot or the location at which the electrode layer is placed. Thus, the partially oxidized thin layer graphite piece layer or the partially reduced thin layer graphite piece layer subjected to a reduction treatment of the present invention preferably has a surface resistivity Ra with a coefficient of variation CV of 10% or less, as measured before physical contact, that is, before tape peeling of the thin layer graphite layer is carried out simulating the peeling due to physical contact described above. The coefficient of variation CV is a value (expressed in %) obtained by dividing a standard deviation by the arithmetic mean and multiplying the quotient by 100, and smaller CVs indicate smaller variations in electrical conductivity, meaning that the surface of the partially oxidized thin layer graphite piece layer serving as an electrode layer has more uniform electrical conductivity. CV is more preferably 5% or less, particularly preferably 3% or less. The coefficient of variation CV can be determined by the method in Section C in Examples below.

Even upon physical contact in use, such as being rubbed and hit, the thin layer graphite site at the physical contact point will not be lost completely but remain on the substrate since the layer comprising partially oxidized thin layer graphite pieces is bonded to the substrate via a chemical bond. Consequently, the surface resistivity of the site tends to be higher as compared to before the physical contact. This change in surface resistivity is preferably small. That is to say, when tape peeling is performed to evaluate the resistance to peeling due to physical contact, the ratio Rr (=Rb/Ra) of the surface resistivity Rb after tape peeling to the surface resistivity Ra of the partially oxidized thin layer graphite piece layer of the present invention, preferably, to the surface resistivity Ra before tape peeling of the partially reduced thin layer graphite piece layer subjected to a reduction treatment is preferably 1 to 100. Although Rb is larger than Ra, the change (Rr) of 1, or more than 1 and closer to 1, means higher retention of electrically conductive properties. Hence, Rr is more preferably 10 or less. The tape peeling and Rr were carried out and determined by the method of Section B in Examples below.

The average thickness ta of the partially oxidized thin layer graphite piece layer is set to be a thickness such that physical properties required in applications of the laminate of the present invention, for example, an electrode material, a heat sink material, or a gas barrier material described below are exhibited, that is, a thickness preferred for the layer comprising partially oxidized thin layer graphite pieces to exhibit high electrical conductivity, thermal conductivity, or gas barrier layer. Although the layer comprising thin layer graphite pieces is preferably thinner to be stably formed, it is preferably thick to some degree to be homogeneous and have stable physical properties, and thus the average thickness ta is 3.0 nm to 10,000 nm. When the laminate of the present invention is used as an electrode material, the average thickness ta of the partially oxidized thin layer graphite piece layer or the partially reduced thin layer graphite piece layer subjected to a reduction treatment is preferably 5.0 nm to 1,000 nm so that the electrode layer can have a smooth surface and a surface resistivity Ra, as measured before tape peeling, with a small variation. When the partially oxidized thin layer graphite layer is formed for electrode layer applications, the average thickness ta is particularly preferably 10 nm to 500 nm to allow the layer to be formed in a single coating without the need for recoating or other processes.

In the case of use as a heat sink material, the heat sink material, similarly to the above-described substrate, preferably conforms to the shape of a place where it is used, and thus ta is preferably 5.0 nm to 5,000 nm. To allow sufficient heat dissipation, ta is particularly preferably 10.0 nm to 1,000 nm.

For the patterning for an electrode material and a heat sink material, combinations of pattern printing using a coating agent containing partially oxidized thin layer graphite pieces, pattern formation using an ink-jet process, and other methods, or patterning of a solid electrode by photolithography or laser ablation can be used. These methods are extremely useful in processing the laminate of the present invention into a device.

When the laminate of the present invention is used as a gas barrier material, ta is preferably 5.0 nm to 5,000 nm to achieve sufficient gas barrier properties. In particular, when the laminate is used as an inner tube in a high-pressure gas tank, for example, ta is particularly preferably 10 nm to 1,000 nm to enable a large capacity. The average thickness ta of an electrode layer can be determined using a scanning electron microscope, a laser microscope, or by the observation method in Section D below using a transmission electron microscope.

The partially oxidized thin layer graphite piece layer in the laminate of the present invention preferably contains partially oxidized thin layer graphite pieces in an amount of 95.0% by mass or more, more preferably 98.0% by mass or more, particularly preferably 99.0% by mass or more, most preferably 99.5% by mass or more. The thin layer graphite refers to a graphene sheet having a structure of a single layer or a laminate of two or more layers. The graphene sheet is a two-dimensional honeycomb assembly of great numbers of lattice structures of hexagonal benzene rings formed by carbon-carbon $\pi$-bonds. When partially oxidized thin layer graphite pieces constitute the partially oxidized thin layer graphite piece layer in the laminate of the present invention, pieces of partially oxidized thin layer graphite are laminated to each other. The layers of partially oxidized thin layer graphite may be bonded to each other by $\pi$-$\pi$ intermolecular forces alone or may be partially connected to each other via an interlayer chemical bond other than a covalent bond or a noncovalent bond.

The partially oxidized thin layer graphite piece layer is preferably a layer substantially free of a binder and made of partially oxidized thin layer graphite pieces alone. The binder as used herein refers to a material made of a component other than partially oxidized thin layer graphite pieces and used to strengthen the bonding of thin layer graphite pieces to retain the form of the thin layer graphite piece layer. The thin layer graphite pieces of the present invention, for having oxygen-containing functional groups as described below, can attract each other to form a robust thin layer graphite piece layer made of thin layer graphite pieces alone. Furthermore, being substantially free of a binder enables a dense chemical structure in which thin layer graphite pieces are compacted, which provides a thin layer graphite piece layer with higher electrical conductivity, thermal conductivity, and gas barrier properties.

The partially oxidized thin layer graphite piece layer in the laminate of the present invention can contain other materials in addition to thin layer graphite pieces to the extent that the excellent substrate adhesion of the laminate of the present invention or the electrical conductivity, thermal conductivity, or gas barrier properties of the laminate of the present invention in use are not adversely affected. Examples of other materials include additives such as flame retardants, lubricants, antioxidants, crystal nucleating agents, and end-capping agents; particulate, rod-shaped, and fibrous metal fine particles; and carbonaceous fine particles such as furnace black, Ketjen black, acetylene black, and carbon nanotubes. These may be added in a small amount of 5% by mass or less. In particular, regarding carbon nanotubes, single-walled carbon nanotubes and double-walled carbon nanotubes have a small tube diameter and high electrical conductivity. In addition, carbon nanotubes have a high affinity for the thin layer graphite pieces used in the present invention and thus is dispersed well in the coating agent of the present invention in the presence of the thin layer graphite pieces.

When the laminate of the present invention is used as an electrode material, carbon nanotubes are suitable for combined use to provide further improved electrical conductivity. In this case, the amount of single-phase and/or double-walled carbon nanotubes in the coating agent is preferably 5% by mass or less based on 100% by mass of thin layer graphite to produce a sufficient electrical conductivity-improving effect while maintaining good dispersibility with a slight addition. In addition to these additives and carbonaceous fine particles, impurities such as oxides and salts of boron (B), nitrogen (N), sulfur (S), sodium (Na), potassium (K), manganese (Mn), silicon (Si), and aluminum (Al) may be added in an amount of, for example, 5% by mass or less, more preferably 2% by mass or less, particularly preferably 1% by mass or less, most preferably 0.5% by mass or less. The amount of these impurities in the partially oxidized thin layer graphite piece layer can be determined by the method of Section F in Examples below.

In the laminate of the present invention, the substrate constituting the laminate and the partially oxidized thin layer graphite piece layer on the substrate are bonded to each other via a first chemical bond. Because of the bonding via a chemical bond, the thin layer graphite piece layer, even if brought into physical contact during use to undergo peeling or wear, will not be lost completely at the physical contact site and remain on the substrate, whereby the change in physical properties such as electrical conductivity, thermal conductivity, or gas barrier properties can be minimized. The chemical bond is preferably selected from a covalent bond, an ionic bond, and a hydrogen bond in view of their intrinsic high bonding strength and high heat resistance. The bonding via a chemical bond is particularly preferably via an ionic bond and/or a hydrogen bond because, even if a reduction treatment is performed, the ionic bond and/or the hydrogen bond are strong and can retain the adhesion without little influence from the reduction. One particularly preferred bond is a hydrogen bond between a hydroxyl group of the substrate and a carboxyl group or a hydroxyl group of the partially oxidized thin layer graphite pieces. When a binding agent, which will be described below, is used, an ionic bond between an amino group, an example of a second binding functional group, of the binding agent and a carboxyl group or a hydroxyl group of the partially oxidized thin layer graphite pieces is also a particularly preferred bond. For the formation of a chemical bond, the above-described coating agent and the formation of the layer comprising partially oxidized thin layer graphite pieces through the application of the coating agent will be described first, and then a preferred method for producing the laminate of the present invention will be described.

The layer comprising partially oxidized thin layer graphite pieces in the laminate of the present invention can be formed by applying a coating agent containing at least one type of partially oxidized thin layer graphite pieces as described below or casting the coating agent in a mold, and then removing an unnecessary dispersion medium. The coating agent contains a dispersion medium and at least one type of partially oxidized thin layer graphite pieces and may optionally contain a dispersant, a binder, and other additives.

The dispersion medium used for the coating agent may be any medium that allows partially oxidized thin layer graphite pieces to be homogeneously dispersed in the coating agent and allows a coating agent viscosity suitable for a process for forming a thin layer graphite piece layer. Examples include water, organic solvents, such as ethanol and N-methyl-2-pyrrolidone (NMP), monomers, prepolymers, and polymers. Water and organic solvents, such as methanol, ethanol, isopropanol, tetrahydrofuran, acetone, N,N-dimethylformamide (DMF), dimethylacetamide, dimethyl sulfoxide (DMSO), and NMP, which are highly volatile and can readily be removed, are preferred. Of these, water, ethanol, isopropanol, and NMP are particularly preferred. These dispersion media may be used alone or, if necessary, as a mixture of two or more media in order, for example, to improve the dispersibility of the partially oxidized thin layer graphite pieces of the invention. In a mixed solvent, however, the dispersibility may contrarily be low when the dispersibilities of the partially oxidized thin layer graphite pieces in the two or more media are not necessarily at the same level, and thus it is preferable to use a single dispersion medium alone.

Next, as the partially oxidized thin layer graphite pieces in the coating agent, pieces synthesized using at least one material selected from gases, liquids, and solids from the atom level in a bottom-up manner by chemical and/or physical syntheses can be used. Preferably, partially oxidized thin layer graphite prepared through chemical and/or physical thin-layering processes using a carbon material having a graphite structure, such as natural graphite, artificial graphite, expanded graphite, or a graphite sheet, as a raw material is can be used in the form of a flat piece having a size large enough relative to thickness.

A description will now be given of a specific thin-layering process for preparing partially oxidized thin layer graphite pieces using a carbon material having a graphite structure.

For chemical thin-layering, an organic synthetic method or a high energy application method, such as plasma application or microwave application, can be performed on natural graphite or artificial graphite. In these methods, the graphite material, such as natural graphite or artificial graphite, is functionalized to force apart graphene sheet layers constituting the material, and the graphene sheets are delaminated to achieve thin-layering.

In particular, chemical thin-layering using a high energy application method, such as plasma application or microwave application, is preferred. For plasma application, atmospheric-pressure plasma and low-pressure plasma can be used. Plasma treatment can be carried out in a gas or a liquid using a highly durable metal, such as gold, platinum, or tungsten, as an electrode to achieve chemical thin-layering. Likewise, microwave treatment can be carried out in a gas or a liquid. As an atmosphere gas, air can be used as it is; alternatively, air is replaced with a gas such as carbon dioxide, ammonia, oxygen, or nitrogen, and then the gas can be used alone or as mixed with a plurality of gases including air in a desired ratio. When a liquid is used, microwave treatment can be carried out using water or an organic solvent, such as ethyl alcohol or NMP, to provide partially oxidized thin layer graphite pieces.

Organic synthetic methods, which can sufficiently add oxygen-containing functional groups described below, can also be used for chemical thin-layering. There are many known organic synthetic methods, and typical examples of preferred methods include Brodie method, which involves oxidizing graphite in concentrated nitric acid using potassium chlorate as an oxidizing agent, followed by treatment with water; Staudenmaier method, which involves placing graphite in a mixed solution of nitric acid and sulfuric acid and oxidizing the graphite with potassium chlorate; Hummers method, which involves placing graphite in cooled concentrated sulfuric acid containing sodium sulfate, stirring the solution until homogeneous, and then adding potassium permanganate to oxidize the graphite; improved versions of these organic synthetic methods; and other chemical methods of dispersion preparation involving contacting a graphite material with fuming sulfuric acid and/or fuming nitric acid. Of these methods, Hummers method or an improved Hummers method, which uses natural graphite, artificial graphite, or expanded graphite as a raw material, is particularly preferred in terms of industrial use because the reaction is mildest, so that thin-layering proceeds efficiently, and, in addition, the degree of oxidation described below can readily be controlled. After the reaction, the resulting reaction solution is centrifuged or filtered to remove unwanted impurities such as metal compounds, metal ions, and acid ions, whereby a dispersed solution of partially oxidized thin layer graphite pieces is obtained.

Physical thin-layering will now be described. For physical thin-layering, various mills can be used. Examples of mills include media-type thin-layering apparatuses, such as planetary ball mills and mixer mills that reciprocate substantially linearly at a high speed; and media-less mills, such as disk mills like stone mills, dry-type (powder) and wet-type (dispersion and other wet forms) rotor mills that use high-speed rotating blades and centrifugal force, and wet-type jet mills having small holes through which materials are passed at a high speed under a high pressure. Using these apparatuses, partially oxidized thin layer graphite pieces can be prepared from a graphite sheet and expanded graphite as well as natural graphite and artificial graphite. Graphite sheet is prepared by infusibilizing a resin in the form of a film in an inert atmosphere at approximately 500° C. to 1,200° C. and then burning the resin at approximately 1,500° C. to 3,300° C. The graphite sheet is first processed into coarse-grained pieces using an apparatus such as a knife mill or a crushing mill and then further subjected to a physical thin-layering process. Expanded graphite is formed by heat-treating acid-treated graphite under the conditions of high-speed heating and a high temperature to expand the graphite several hundred fold and force graphite layers apart. Acid-treated graphite is prepared by immersing graphite in a solution containing an acidic substance and an oxidizing agent to produce a graphite intercalation compound and then washing and drying the compound.

The heat treatment under the conditions of high-speed heating and a high temperature can be carried out in a high-temperature furnace at 500° C. or higher or by rapid heating with microwaves. In particular, rapid heating with microwaves, which gives a great expansion, is a preferred method. The physical thin-layering process can be carried out using a raw material alone, in the copresence of a polymer or a dispersion medium constituting the coating agent for the application described below, or using a mill after a composite of a raw material and a polymer is once formed.

In addition to the above-described mills, kneading extruders equipped with one or more than one screw shaft can be used for physical thin-layering. Kneading is performed in the copresence of a relatively viscous medium, for example, a plastic polymer, and then the medium is removed to prepare thin layer graphite pieces. In this method, the shear force of a screw drives peeling. In particular, when the medium is a polymer and has thermoplasticity and viscoelasticity, the viscoelasticity and the shearing effect of a screw can effectively cause peeling, thereby achieving thin-layering. As an apparatus for kneading, multi-screw extruders equipped with two or more shafts are suitable for use because thin layer graphite pieces, when kneaded with a medium, can be efficiently thin-layered while being kneaded. To knead the thin layer graphite pieces and the medium more homogeneously, it is preferable to use a powder material or a powdered thermoplastic polymer.

Examples of preferred physical thin-layering processes include thin-layering in a planetary ball mill in the presence of a carbon material alone, thin-layering with a rotor mill in the copresence of a dispersant, wet-type thin-layering with a jet mill in the copresence of a dispersant, thin-layering in a mixer mill in the copresence of a carbon material, a solvent, and a prepolymer, and thin-layering by shear force while kneading a carbon material with a thermoplastic polymer using a multi-screw kneader equipped with two or more screw shafts. Wet-type thin-layering with a rotor mill in the presence of a dispersant and wet-type thin-layering with a jet mill in the presence of a dispersant are particularly preferred. The carbon material is most preferably expanded graphite. Partially oxidized thin layer graphite pieces thin-layered by subjecting expanded graphite to a physical thin-layering process can be used.

These physical thin-layering processes, as compared to chemical thin-layering processes, tend to provide less oxidized partially oxidized thin layer graphite pieces. It is preferable to perform a chemical thin-layering process in combination after a physical thin-layering process is performed. This is because more effective oxidation and thin-layering associated therewith can be achieved, and the dispersibility of partially oxidized thin layer graphite pieces in the coating agent improves. A particularly preferred thin-layering process is to subject natural graphite or expanded graphite to a physical thin-layering process using a planetary ball mill and then perform Hummers method or an improved Hummers method.

Among these methods for preparing partially oxidized thin layer graphite pieces, chemical thin-layering is preferred, and chemical thin-layering by an organic synthetic method is particularly preferred. Most preferred is chemical thin-layering by Hummers method or an improved Hummers method using natural graphite, artificial graphite, or expanded graphite as a raw material. These chemical thin-layering processes are more preferably performed in combination to effectively achieve thin-layering. Specifically, a more preferred thin-layering process is to subject natural graphite or expanded graphite to a microwave treatment in the air and then perform Hummers method or an improved Hummers method.

Partially oxidized thin layer graphite pieces obtained by a chemical or a physical thin-layering process have oxygen-containing functional groups, specifically, highly polar functional groups containing an oxygen atom, such as a hydroxyl group (—OH), a carboxyl group (—COOH), an ester bond (—C(=O)—O—), an ether bond (—C—O—C—), a carbonyl group (—C(=O)—), and an epoxy group. The partially oxidized thin layer graphite pieces having oxygen-containing functional groups have an improved affinity for dispersion media in a coating agent where the pieces are dispersed. Functionalization further facilitates thin-layering to improve the dispersibility of the pieces in the dispersion medium. Thus, the coating agent itself is provided with excellent coating properties, and a thin and highly smooth layer comprising partially oxidized thin layer graphite pieces can be formed. The partially oxidized thin layer graphite pieces at this point after the chemical thin-layering process described above contain an appropriate amount of oxygen-containing functional group and has become suitable for dispersion, and the degree of oxidation (O/C) of the pieces is preferably 0.17 to 0.85, more preferably 0.25 to 0.75. When the pieces are subjected to a reduction treatment as described below, the lower the degree of oxidation is, the more the oxygen-containing functional groups are lost to restore the π electronic conjugated structure of the thin layer graphite pieces, leading to higher electrical conductivity. Thus, the degree of oxidation is particularly preferably 0.30 to 0.65.

To control the dispersibility in the coating agent or improve the properties (e.g., electrical conductivity) of the partially oxidized thin layer graphite pieces themselves, the partially oxidized thin layer graphite pieces may be reduced to have a decreased amount of oxygen-containing functional group. The decreased amount of oxygen-containing functional group is preferred because it allows the partially oxidized thin layer graphite pieces to be easily dispersed more in organic solvent than in water, leading to so improved coating properties that the coating agent is uniformly applied to the substrate, providing a thin and highly smooth layer comprising partially oxidized thin layer graphite pieces. The reduction treatment can be carried out using various methods, including chemical reduction using a reducing agent, such as sodium borohydride ($NaBH_4$) or hydrazine ($N_2H_4$); thermal reduction using a light source, such as laser light or flashlight, or electromagnetic waves, such as ultraviolet rays or microwaves; and heat reduction by heating at 100° C. or higher in an inert atmosphere.

Chemical reduction using a highly reducing agent, such as hydrazine, sodium hydroxide, or sodium dithionite, readily achieves a desired degree of oxidation. Highly reducing agents, such as hydrazine, sodium hydroxide, and sodium dithionite, are particularly preferred also in that they can dissolve the required amount as a solute and reduce the partially oxidized thin layer graphite pieces in the solution. The partially oxidized thin layer graphite pieces at this point after the reduction have a significantly decreased amount of oxygen-containing functional group and has become suitable for dispersion and the application described below, and the degree of oxidation (O/C) of the pieces is preferably 0.07 to 0.85, more preferably 0.08 to 0.75. The degree of oxidation is particularly preferably 0.09 to 0.65 because when the reduction treatment is performed again after the application as described below, the oxygen-containing functional groups are lost, while the π electronic conjugated structure of the thin layer graphite pieces is restored, resulting in higher electrical conductivity.

The partially oxidized thin layer graphite pieces obtained by the above-described physical thin-layering process have the above-described oxygen-containing functional group, but in a small proportion, and preferably has a degree of oxidation (O/C) of 0.07 to 0.20.

As described above, partially oxidized thin layer graphite pieces in the coating agent are preferably obtained by the chemical and/or physical thin-layering described above; more preferred are those to which oxygen-containing functional groups are added; and particularly preferred are those to which oxygen-containing functional groups are added by chemical thin-layering.

To provide partially oxidized thin layer graphite pieces with improved dispersibility in coating agents or provide a layer comprising thin layer graphite pieces with improved flatness, electrical conductivity, thermal conductivity, or gas barrier properties, different types of partially oxidized thin layer graphite pieces may be used. In this case, it is particularly preferable to use, as partially oxidized thin layer graphite pieces to which oxygen-containing functional groups are added obtained by the chemical thin-layering process described above, two types of partially oxidized thin layer graphite pieces having different degrees of oxidation dispersed in water. Furthermore, when two types of partially oxidized thin layer graphite pieces having different degrees of oxidation are used in combination as partially oxidized thin layer graphite pieces obtained by the chemical thin-layering process described above, it is also preferable to use reduced partially oxidized thin layer graphite pieces as partially oxidized thin layer graphite pieces having a lower degree of oxidation and NMP as a dispersion medium. In this case, the partially oxidized thin layer graphite pieces having a lower degree of oxidation, although having high electrical conductivity, may have poor dispersibility in the coating agent or poor adhesion to the substrate. The partially oxidized thin layer graphite pieces having a higher degree of oxidation have a high affinity for dispersion media. The partially oxidized thin layer graphite pieces having a higher degree of oxidation are highly dispersible in water, alcohols, and NMP, which are suitable as dispersion media. In addition, the partially oxidized thin layer graphite pieces having a higher degree of oxidation also have a high affinity for the partially oxidized thin layer graphite pieces having a lower degree of oxidation. Furthermore, the partially oxidized thin layer graphite pieces having a higher degree of oxidation also have high adhesion to the substrate. Therefore, the partially oxidized thin layer graphite pieces having a higher degree of oxidation also function as a dispersant or a binder of the partially oxidized thin layer graphite pieces having a lower degree of oxidation. Consequently, the partially oxidized thin layer graphite pieces having a lower degree of oxidation has improved dispersibility in a dispersion medium. This can result in a coating solution having excellent coating properties and, moreover, the formation of a preferred laminate excellent in conductivity, smoothness, and adhesion to the substrate.

In the laminate of the present invention, the average thickness T of the partially oxidized thin layer graphite pieces in the coating agent for forming the layer comprising partially oxidized thin layer graphite pieces is preferably as small as possible. This is because partially oxidized thin layer graphite pieces having such an average thickness T are dispersed well in a dispersion medium, leading to reduced coarse grains and excellent coating properties. The thickness of a partially oxidized thin layer graphite piece means a size, i.e., a thickness, in the direction perpendicular to the plane of a planar structure of the thin layer graphite piece. The average thickness T of the thin layer graphite pieces is preferably 0.3 nm to 100 nm, more preferably 0.6 nm to 50 nm to provide a coating agent with good coating properties, particularly preferably 1.0 nm to 30 nm to minimize coarse grains to facilitate process control. In addition to the foregoing advantages, in terms of economic advantages, the average thickness T is most preferably 1.5 nm to 20 nm. The average thickness T of thin layer graphite pieces can be determined using a scanning electron microscope, a laser microscope, or by the method described in Section D in Examples below using a transmission electron microscope.

In the laminate of the present invention, the average size L of the partially oxidized thin layer graphite pieces in the coating agent for forming the layer comprising partially oxidized thin layer graphite pieces is preferably 0.1 μm to 200 μm. Within this range, the dispersibility of the partially oxidized thin layer graphite pieces in the coating agent is advantageously good. An excessively large average size L may result in poor dispersibility in the coating agent. The average size L is more preferably 0.1 μm to 100 μm, particularly preferably 0.5 μm to 50 μm, most preferably 1.0

µm to 30 µm. The average size L of partially oxidized thin layer graphite pieces can be determined using a light microscope, an atomic force microscope, or by the observation using a laser microscope in Section E in Examples below.

The above-described coating agent containing partially oxidized thin layer graphite pieces can contain a dispersant for uniformly dispersing the partially oxidized thin layer graphite pieces in the coating agent to the extent that the formation of the layer comprising partially oxidized thin layer graphite pieces is not inhibited. Specific examples include nonionic surfactants, such as aromatic ether, carboxylic acid ester, acrylic acid ester, phosphoric acid ester, sulfonic acid ester, fatty acid ester, urethane, fluorine, aminoamide, acrylamide, and polyalkylene glycol surfactants; cationic surfactants, such as phosphonium-containing polymer, aromatic amine, and aliphatic amine surfactants; and anionic surfactants, such as carboxylic acid, phosphoric acid, sulfonic acid, hydroxy fatty acid, and fatty acid amide surfactants. Of these, polyalkylene glycol, phosphoric acid ester, aromatic amine, and aliphatic amine surfactants are preferred because they have a high affinity for thin layer graphite pieces in a coating agent to stabilize the dispersibility of the thin layer graphite pieces in the formation of the layer comprising partially oxidized thin layer graphite pieces by application. Polyalkylene glycol (e.g., polyethylene glycol) surfactants and aromatic amine (e.g., catecholamines and salts thereof) surfactants are more preferred.

The above-described coating agent containing partially oxidized thin layer graphite pieces, after being prepared by mixing the partially oxidized thin layer graphite pieces with a dispersion medium, is loaded directly onto the substrate in the present invention or onto a preferred binding agent described below. For the mixture to prepare the coating agent, ultrasonic homogenizers, planetary ball mills, mixer mills, rotor mills, jet mills, or other apparatuses can be used. Of these, ultrasonic homogenizers, rotor mills, and jet mills are preferred. The mixing ratio of the partially oxidized thin layer graphite pieces to the dispersion medium is preferably selected such that the coating agent, when applied to the binding agent, has an appropriate viscosity. The amount of partially oxidized thin layer graphite pieces in the coating agent is preferably 0.01% by mass to 10% by mass, particularly preferably 0.1% by mass to 5.0% by mass to form a partially oxidized thin layer graphite piece layer having a desired thickness in one single application. For the application to the substrate or the binding agent, coaters are used. Coaters such as die coaters, bar coaters, applicators, spray coaters, spin coaters, and ink jet coaters are suitable for use. However, dip coating, which can hardly achieve uniform coating, is not used.

A description will now be given of a preferred method for producing the laminate of the present invention. In the method for producing the laminate of the present invention, as described above, a coating agent containing partially oxidized thin layer graphite pieces is directly loaded onto a substrate, and the substrate and the partially oxidized thin layer graphite pieces are chemically bonded to each other to provide the laminate of the present invention. To ensure that the chemical bond is formed, preferably, a binding agent having a first binding functional group that forms a chemical bond with the substrate and a second binding functional group that forms a chemical bond with the partially oxidized thin layer graphite pieces is loaded onto the substrate; the coating agent containing partially oxidized thin layer graphite pieces is loaded; and the binding agent is chemically bonded to the substrate and to the thin layer graphite piece layer to provide the laminate of the present invention. In other words, in the laminate thus produced, the substrate and the layer comprising thin layer graphite pieces are bonded to each other in direct contact with the material of the substrate, preferably, via a binding agent having a first chemical bond with the substrate made of a polymer material and a second chemical bond with reduced partially oxidized thin layer graphite pieces (partially reduced thin layer graphite pieces).

A preferred binding agent will be described. The chemical bond between the first binding functional group of the binding agent and the substrate can be formed at a stage before the subsequent loading of the coating agent containing at least one type of partially oxidized thin layer graphite pieces onto the binding agent. The formation of the chemical bond at a stage before applying the coating agent containing partially oxidized thin layer graphite pieces allows the binding agent to be firmly loaded on the substrate and further allows the bond between the partially oxidized thin layer graphite pieces and the binding agent via the second binding functional group to be stably and rapidly formed by the subsequent application of the coating agent.

The chemical bond between the first binding functional group of the binding agent and the substrate is preferably a covalent bond or an ionic bond or both to be readily formed by the application of the binding agent to the substrate. Examples of preferred covalent bonds include an ether bond (—C—O—C—), which formed by the dehydration of hydroxyl groups; an amide bond (—CO—NH—), which is formed by dehydration condensation of an amine and a carboxylic acid; an ammonium group (—$NH_3^+$ and $O_2^-C$—); an ester bond (—C(=O)—O—), which is formed by the dehydration condensation of a hydroxyl group and a carboxylic acid; a silyl ether bond (—Si—O—C—), which is formed by the dehydration condensation of a hydroxyl group and a silanol group formed through the hydrolysis of an alkoxysilane; and a thiolate bond (—C—S-M-; where M is a functional group of the substrate), which is formed from a thiol group. Examples of the first binding functional group that gives such a covalent bond include a hydroxyl group, an amino group, an ammonium group, a carboxyl group, alkoxysilane, and thiol. In particular, an alkoxysilyl group is preferred because hydrolysis is readily effected by moisture in the air, and the reaction is readily promoted by heating at a relatively low temperature, and an amino group and an ammonium group are preferred because they readily and strongly form a bond with a hydroxyl group, a carboxyl group, or a salt thereof. The first binding functional group is particularly preferably an alkoxysilyl group. Prior to the above-described application of the binding agent to the substrate, the substrate is preferably subjected to a physical and/or chemical pretreatment. When the substrate is a polymer material, the physical pretreatment is particularly preferably UV ozonation or atmospheric-pressure plasma treatment.

In the preferred method for producing the laminate of the present invention, the laminate can be produced by forming a chemical bond between the substrate and the binding agent via the first binding functional group as described above, applying the coating agent containing at least one type of partially oxidized thin layer graphite pieces to the binding agent, and then forming a chemical bond via the second binding functional group. The chemical bond between the second binding functional group of the binding agent and the thin layer graphite pieces in the layer comprising partially oxidized thin layer graphite pieces is preferably formed readily and strongly. The chemical bond is preferably selected from a covalent bond, an ionic bond, and a hydrogen bond. Of these, at least one selected from an ionic bond and a hydrogen bond is particularly preferred. When the partially oxidized thin layer graphite pieces are partially oxidized thin layer graphite pieces to which oxygen-containing functional groups are added obtained by chemical thin-layering, which are preferred as described above, the chemical bond between the second binding functional group of the binding agent and the thin layer graphite pieces in the layer comprising partially oxidized thin layer graphite pieces is particularly preferably at least one bond selected from an ionic bond and a hydrogen bond because the electrical conductivity can be enhanced by the reduction treatment described below. In this case, the covalent bond, the ionic bond, or the hydrogen bond is less likely to be broken by the reduction treatment. In particular, the ionic bond and the hydrogen bond are retained without little influence from the reduction treatment. In particular, in the partially oxidized thin layer graphite pieces having oxygen-containing functional groups, some of the functional groups are carboxyl groups, sulfonic groups, or hydroxyl groups. Carboxyl groups and sulfonic groups, when in a coating agent, partially dissociate depending on the dissociation constant and are present in the form of carboxylate ions ($RCOO^-$) and sulfonic acid ions ($R-SO_3^-$), and hydroxyl groups readily form hydrogen bonds. Thus, the second binding functional group is more preferably a basic functional group such as an amine, which can form a strong ionic bond or hydrogen bond with these groups, or an ester group (—C(=O)—O—), which has a high affinity for carboxyl groups and hydroxyl groups. Preferred basic functional groups include primary amines, secondary amines, and tertiary amines, and an ammonium group (quaternary ammonium group) is also preferred. Other examples of the second binding functional group suitable for use include epoxy groups, such as a glycidyl ether group, a glycidyl ester group, and a glycidyl amine group, a vinyl group, and an isocyanate group, which groups can form a covalent bond with the partially oxidized thin layer graphite pieces upon the application of physical energy such as heat or electromagnetic waves.

The chemical bond between the partially oxidized thin layer graphite pieces and the binding agent via the second binding functional group is formed gradually as a dispersion medium in the coating agent applied to the binding agent is removed naturally or by the additional use of a technique such as heating, or formed by physical energy application, such as heating or electromagnetic irradiation, after the dispersion medium has been removed from the coating agent. The gradual formation as the dispersion medium is removed from the coating agent by heating is preferred. The chemical bond via the second binding functional group is preferably formed by removing the dispersion medium by heat treating the coating agent applied preferably at 40° C. to 150° C. for 5 seconds to 15 minutes in the air.

The binding agent that can be used in the process for producing the laminate of the present invention is a molecule having the first binding functional group, which forms a chemical bond with the substrate, and the second binding functional group, which forms a chemical bond with the partially oxidized thin layer graphite pieces, as described above. The binding agent has at least one first binding functional group and at least one second binding functional group in one molecule. Larger numbers of these binding functional groups in one molecule facilitate the formation of the chemical bonds, and thus the numbers of the binding functional groups in one molecule of the binding agent are preferably more than one. In addition to the first binding functional group and the second binding functional group, the binding agent may have another functional group in its molecule. To further ensure that the substrate and the partially oxidized thin layer graphite piece layer can tightly adhere to each other, the first binding functional group and the second binding functional group in the binding agent are preferably close to each other in chemical structure, and the first binding functional group and the second binding functional group are preferably arranged at the shortest distance of ten atoms or less. For example, in the case of 3-aminopropyltrimethoxysilane (structure: $H_2NC_3H_6Si(OCH_3)_3$), a preferred binding agent described below, the silicon atom of trimethoxysilane, the first binding functional group, and the N atom of primary amine, the second binding functional group, are arranged at the shortest distance of three carbon atoms.

Examples of preferred molecular structures of the binding agent suitable for use in the process for producing the laminate of the present invention include silicon compounds, including compounds having a vinyl group and an alkoxysilane, such as vinyltrimethoxysilane, vinyltriethoxysilane, vinyltriacetoxysilane, allyltrimethoxysilane, vinyltris(2-methoxyethoxy)silane, p-styryltrimethoxysilane, 3-acryloxypropyltrimethoxysilane, 3-methacryloxypropyltrimethoxysilane, 3-methacryloxypropyltriethoxysilane, 3-methacryloxypropylmethyldimethoxysilane, and 3-methacryloxypropylmethyldiethoxysilane; compounds having an epoxy group and an alkoxysilane, such as 3-glycidoxypropyltrimethoxysilane, 3-glycidoxypropyltriethoxysilane, 3-glycidoxypropylmethyldimethoxysilane, 3-glycidoxypropylmethyldiethoxysilane, and 2-(3,4-epoxycyclohexyl)ethyltrimethoxysilane; compounds having an isocyanate group and an alkoxysilyl group, such as 3-isocyanatepropyltrimethoxysilane and 3-isocyanatepropyltriethoxysilane; and compounds having an amino group and an alkoxysilyl group, such as 3-aminopropyltrimethoxysilane, 3-aminopropyltriethoxysilane, 3-(2-aminoethyl)aminopropyltrimethoxysilane, and N-(2-aminoethyl)-3-aminopropylmethyldimethoxysilane. Other examples include thiol compounds, including aminoalkanethiols such as aminomethanethiol, 2-aminoethanethiol, 2-aminobenzenethiol, 3-amino-1-propanethiol, 1-amino-2-propanethiol, 4-amino-1-butanethiol, 2-amino-4-phenyl-1-butanethiol, 6-amino-1-hexanethiol, (S)-1-aminopentane-2-thiol, 5-aminopentane-1-thiol, 6-amino-1-hexanethiol, 6-(dimethylamino)-1-hexanethiol, and 7-amino-1-heptanethiol.

Other examples include polymer binding agents such as allylamine polymers, amidoamine polymers, ester polymers, vinyl alcohol polymers, and acrylic polymers, which have many functional groups in their molecules and are provided with properties suitable for application. As compounds having a preferred dialkoxysilyl group and trialkoxysilyl group, which can readily and strongly form a bond with a polymer material, as the first binding functional group and a basic functional group, which can readily form an ionic bond with an oxygen-containing functional group, as the second binding functional group as described above, compounds having an organic group to which an alkoxysilyl group and an amino group are bound are preferred. Examples include 3-aminopropyltrimethoxysilane, 3-aminopropyltriethoxysilane, 3-(2-aminoethyl)aminopropyltrimethoxysilane, N-(2-aminoethyl)-3-aminopropyltrimethoxysilane, and N-(2-aminoethyl)-3-aminopropylmethyldimethoxysilane. Particularly preferred polymer binding agents are ester polymers and acrylic polymers. These polymers allow a chemical structure having high affinities for both the substrate and the partially oxidized graphite pieces to be easily designed and can easily be applied.

An easy-adhesion film for partially oxidized graphite of the present invention comprises a substrate and a binding agent on the substrate, the agent having a basic functional group and a functional group selected from the group consisting of a hydroxyl group, an amino group, a carboxyl group, and alkoxysilanes. Providing a thin layer graphite piece layer on the binding agent layer on the substrate of the easy-adhesion film for partially oxidized graphite pieces by the method described below can readily provide a thin laminate having high planar homogeneity and substrate adhesion and excellent in electrical conductivity, thermal conductivity, gas barrier properties, and handleability.

The partially oxidized thin layer graphite pieces prepared through the above-described chemical and/or physical thin-layering processes are preferably subjected to a reduction treatment after being loaded in the form of a coating agent onto the substrate or, when the above-described preferred binding agent is employed, after the above-described chemical bond via the second binding functional group is formed. In the reduction, some of the oxygen atoms of oxygen-containing functional groups added to the partially oxidized thin layer graphite pieces are lost. As a result, reduced partially oxidized thin layer graphite pieces become partially reduced thin layer graphite pieces to improve electrical conductivity, heat sink properties, and gas barrier properties against a specific type of gas, and a layer comprising the partially reduced thin layer graphite pieces has a metallic luster. The reduction treatment can be carried out using various methods, including chemical reduction using a reducing agent, such as sodium borohydride ($NaBH_4$) or hydrazine ($N_2H_4$); thermal reduction using a light source, such as laser light or flashlight, or electromagnetic waves, such as ultraviolet rays or microwaves; and heat reduction by heating at 100° C. or higher in an inert atmosphere. Of these, chemical reduction, which is most unlikely to cause defects due to the elimination of carbon dioxide or other reasons during the reduction, is preferred. Chemical reduction using a highly reducing agent, such as hydrazine, sodium hydroxide, or sodium dithionite, is particularly preferred because the reducing agent can dissolve the required amount as a solute and reduce the partially oxidized thin layer graphite pieces in the solution to achieve a desired degree of oxidation. The degree of oxidation (O/C) of the partially oxidized thin layer graphite pieces suitable for performing a reduction treatment is preferably 0.17 to 0.85, more suitably 0.25 to 0.75. The lower the degree of oxidation is, the more the oxygen-containing functional groups are lost to restore the π electronic conjugated structure of the thin layer graphite pieces, leading to higher electrical conductivity. Thus, the degree of oxidation is particularly preferably 0.30 to 0.65.

In the reduction treatment, the concentration of a reducing agent, as well as the reducing capability of the reducing agent itself, affects the degree of oxidation after the reduction. The degree of oxidation (O/C) of a layer comprising partially reduced thin layer graphite pieces obtained by the reduction treatment is preferably 0.07 to 0.85, more preferably 0.08 to 0.75 to achieve high electrical conductivity, thermal conductivity, and gas barrier properties, particularly preferably 0.09 to 0.13 to achieve very excellent electrical conductivity and thermal conductivity. In the case of use as a gas barrier material, the degree of oxidation (O/C) particularly preferably 0.10 to 0.65 to achieve very excellent gas barrier properties without being influenced by slight impurities.

Combining the above-described reduction method, an appropriate coating method, and an appropriate patterning method under appropriate conditions can provide a laminate having a pattern and a circuit geometry and including a partially oxidized thin layer graphite piece layer and a partially reduced thin layer graphite piece layer. When the degree of oxidation (O/C) of partially oxidized thin layer graphite pieces in a layer is as high as 0.15 or more, insulation properties may be exhibited. Thus, by partially reducing the partially oxidized thin layer graphite piece layer by patterning, a partially reduced thin layer graphite piece layer, which serves as an electrode layer, can be formed to provide an electrode material. The pattern and/or the circuit formed of both the partially oxidized graphite piece layer and the partially reduced thin layer graphite piece layer can be used as any of a heat sink pattern that dissipates heat through a desired route, a pattern that blocks gas only at a desired portion, a gas barrier pattern that permeates gas at a controlled speed, and an electrode and/or an electronic circuit having a desired shape. Furthermore, any two or all three of the heat sink pattern, the gas barrier pattern, and the electronic circuit can be combined to form a laminate, and the laminate can be a highly-functional laminate consisting of a substrate, partially oxidized thin layer graphite pieces, and a substrate.

The laminate of the present invention can take various forms depending on the intended use, and when used as an electrode material or a heat sink material, it preferably takes a sheet form as a whole or has a patterned circuit geometry. The term "sheet form" as used herein refers, in the case of an electrode material, to that the electrode material itself has a flat shape, and the narrowest width portion in the plane direction of the electrode material has a length at least three times as large as a thickness. A sheet form allows mechanical properties, such as a high tensile stress, of the layer comprising partially oxidized thin layer graphite pieces to be exhibited. The patterned circuit geometry refers to that a desired route is formed to send electrical signals or dissipate heat. The laminate is preferably flexible so as to be used in wider applications as an electrode material and a heat sink material and produced by roll-to-roll processes. In the case of an electrode material, for example, the change in surface resistivity before and after being wound up using a roll core with a cross-sectional diameter of 5 cm is preferably as small as possible: preferably 10 times or less, more preferably 5 times or less, particularly preferably 2 times or less. The laminate is preferably in the form of a windable sheet.

The laminate of the present invention, when used as an electrode material, a heat sink material, or a gas barrier material described above, may be used alone or as a plurality of the laminates superposed on each other to further improve the physical properties. To improve physical properties, weather resistance, visibility, and other properties, a surface treatment may be performed. Examples of the surface treatment include surface coating with an organic or inorganic coating agent, planarization processes by pressing or other methods, rubbing processes using a fabric or a roller brush, and imprinting processes using a plate or a roll having microscopic irregularities at the micrometer level to nanometer level on its surface.

Having electrical conductivity, the laminate of the present invention can be used as an electrode material. The electrode material can be used as an electric circuit of a circuit board in various electrical equipment such as information terminal devices or as an element that sends and receives electrical signals in chemical sensors. When the laminate is used as an electrode material, it is preferable to provide, as an electrode layer having an electric circuit geometry as described above, a partially oxidized thin layer graphite piece layer, preferably, a partially reduced thin layer graphite piece layer subjected to a reduction treatment, on a substrate having insulation properties, such as a polyimide film or a polyester film. The partially oxidized thin layer graphite pieces and the partially reduced thin layer graphite pieces each preferably have a degree of oxidation (O/C) of 0.07 to 0.85, more preferably 0.08 to 0.75 to achieve higher electrical conductivity, particularly preferably 0.09 to 0.13 to achieve very high electrical conductivity.

A patterning method for forming an electrode layer will be described. A binding agent is loaded onto a substrate, and then a partially oxidized thin layer graphite piece layer is formed over the whole surface. On the layer, a mask made of a transparent sheet and an electric circuit drawing thereon or a sheet-like mask with portions to be an electric circuit cut off is placed. After that, the partially oxidized thin layer graphite pieces are partially reduced by photoreduction or chemical reduction. Alternatively, the reduction can be carried out by applying a nanosecond, picosecond, or femtosecond low-power laser beam to the laminate produced by forming a layer comprising partially oxidized thin layer graphite pieces over the whole surface while directly drawing an electric circuit. An electrode material in which the portions reduced by any of these methods serve as an electric circuit of the partially reduced thin layer graphite piece layer can be produced.

Alternatively, using the laminate produced by forming a layer comprising partially oxidized thin layer graphite pieces over the whole surface, an electric circuit can be formed by wholly reducing the partially oxidized thin layer graphite into partially reduced thin layer graphite and then removing unnecessary portions with an actinic radiation such as a laser beam having an output power of 0.1 to 2 W.

Alternatively, a mask with portions to be an electric circuit cut off is placed on a substrate, and a binding agent is loaded onto the substrate such that a pattern is formed. After that, a partially oxidized thin layer graphite piece layer is formed at portions where the binding agent is loaded. According to the type of the substrate, a treatment with a light source or chemical reduction is performed, and then the mask is removed; alternatively, the mask is removed, and then a treatment with light or chemical reduction is performed. In particular, it is preferable to perform patterning after the partially oxidized thin layer graphite piece layer is formed. The electrode material is used for various electrical equipment or for cards or chips of electrodes that connect sample contact portions to transducers in chemical sensors, such as ion sensors, bioaffinity sensors, and gas sensors. Chemical sensors including the electrode material of the present invention are advantageously used as electrode materials because in sending and receiving electrical signals output from the properties of test samples to be determined, the sensors hardly react or interact with the test samples to produce little signal noise.

Having thermal conductivity, the laminate of the present invention can be used as a heat sink material. When used as a heat sink material, the laminate is used as a material to dissipate heat in a very small area in household electronic appliances, particularly, personal digital assistants, such as tablet computers and smartphones. A preferred method for producing the heat sink material is described below. A thin substrate having high tensile strength, such as a polyimide film or a polyester film, is provided. On the substrate, a partially oxidized thin layer graphite piece layer that serves as a heat sink portion is formed. More preferably, the partially oxidized thin layer graphite piece layer is subjected to a reduction treatment to form a partially reduced thin layer graphite piece layer. The partially oxidized thin layer graphite pieces or the partially reduced thin layer graphite pieces preferably have a degree of oxidation (O/C) of 0.07 to 0.85, more preferably 0.08 to 0.75 to achieve high thermal conductivity, particularly preferably 0.09 to 0.13 to achieve very high thermal conductivity. Such a heat sink material can be produced as a material patterned by a method as described in the above method for producing an electrode material.

Inside household electronic appliances, a heat sink material is disposed with a partially oxidized thin layer graphite piece layer, preferably, a partially reduced thin layer graphite piece layer subjected to a reduction treatment, being in contact with an integrated circuit, a source of heat. Heat is dissipated to the exterior via the heat sink material. The heat sink material of the present invention effectively dissipates heat. Thus, information terminal devices including the heat sink material of the present invention experience little temperature rise at an integrated circuit in operation or around the integrated circuit and are less likely to malfunction. In addition, the integrated circuit or parts around the integrated circuit are less likely to undergo degradation over time. Furthermore, the heat sink material of the present invention has excellent conformability or tensile stress properties and thus can come into close contact with a heat source to form a heat sink circuit even if the heat source has a large area or a complex shape.

Having gas barrier properties, the laminate of the present invention can be used as a gas barrier material. When used as a gas barrier material, the laminate can be used to block gases, such as water vapor and oxygen, in display units of information terminal devices. The laminate can also be used as an innermost member of a cylindrical tank that is disposed in high-pressure gas tanks, such as LNG tanks for natural gas vehicles and hydrogen gas tanks for fuel cell vehicles, and made of an inner liner resin having gas barrier properties. Typically, in a gas tank, a composite layer, that is, a layer of wound high-strength threads (e.g., carbon fibers) bound with a resin is disposed on the outer surface of the tank made of an inner liner resin. The inner portion and/or the outer portion of an inner liner resin gas tank including a gas barrier material made of the laminate of the present invention are preferably produced by forming a partially oxidized thin layer graphite piece layer directly, or after a binding agent is loaded, over the whole inner surface of a cylindrical substrate made of an inner liner resin layer, such as a polyamide polymer or an ethylene-vinyl alcohol copolymer. In this method, after the partially oxidized thin layer graphite piece layer is formed over the whole inner surface of the cylindrical substrate, the partially oxidized thin layer graphite, depending on the type of gas, may be used as it is without being reduced or may be wholly reduced using a light source or chemical reduction to produce a gas barrier material. The gas barrier material produced can be used for gas tanks for natural gas and hydrogen and, further, for high-pressure gas tanks. In addition to gas tanks, the gas barrier material can be used as an innermost member of supply hoses for tanks, flexible pipes on the periphery of gas storage tanks, and hoses and pipes in infrastructure applications such as gas stations including hydrogen stations. Although not yet fully understood, it is probably that the partially oxidized thin layer graphite pieces and/or the partially reduced thin layer graphite pieces are strongly bonded by a strong interaction therebetween in both the lamination direction (i.e., the thickness direction) of the piece layer and the direction perpendicular to the lamination direction to form a network structure, thus extremely retarding gas permeation. The partially oxidized thin layer graphite pieces and the partially reduced thin layer graphite pieces each preferably have a degree of oxidation (O/C) of 0.07 to 0.85, more preferably 0.08 to 0.75 to achieve high gas barrier properties, particularly preferably 0.10 to 0.65 to achieve very excellent gas barrier properties to form a gas barrier material. In the gas tank, gases are blocked by the partially oxidized thin layer graphite piece layer, and the partially oxidized thin layer graphite piece layer can block gases over a long period of time without being influenced by gases. For gas barrier properties of the gas barrier material, oxygen permeability (oxygen gas barrier properties) can be determined by the method of Section I in Examples below. The value of the oxygen gas barrier properties is preferably 1.0 cc/m$^2$·day or less, more preferably 0.5 cc/m$^2$·day or less. Likewise, hydrogen permeability (hydrogen gas barrier properties) can be determined by the method of Section J in Examples below. The value of the hydrogen gas barrier properties is preferably $1.0 \times 10^{-11}$ cc·cm/cm$^2$·sec·cmHg or less ($7.52 \times 10^{-9}$ cc·cm/cm$^2$·sec·MPa or less), more preferably $5.0 \times 10^{-12}$ cc·cm/cm$^2$·sec·cmHg or less ($3.76 \times 10^{-9}$ cc·cm/cm$^2$·sec·MPa or less), particularly preferably $1.0 \times 10^{-12}$ cc·cm/cm$^2$·sec·cmHg or less ($7.52 \times 10^{-9}$ cc·cm/cm$^2$·sec·MPa or less).

The laminate of the present invention can be used in many applications in addition to the above applications. For example, since the layer comprising partially oxidized thin layer graphite pieces has excellent electrical conductivity, tensile properties in the plane direction of the laminate, and further flexibility, the laminate is suitable for use for strong antistatic packaging materials having electrostaticity or electrical conductivity and electromagnetic-shielding properties, wallpaper having electromagnetic-shielding properties, and building and civil engineering materials, such as materials for repairing buildings, for example, pillars. In particular, a plurality of the laminates of the present invention superposed on each other can be used as a structural material because the layer comprising partially oxidized thin layer graphite pieces sandwiched between the substrates functions as a backbone material.

In addition, the laminate of the present invention, for its substrate adhesion, electrical conductivity, heat resistance, and heat sink properties, can be used as a collecting foil and a heat-resistant separator for batteries. The laminate can also be used as a collecting foil in primary batteries, such as manganese dry batteries, and secondary batteries, such as lithium-ion batteries. In this case, improved adhesion of partially oxidized thin layer graphite pieces to a substrate metal foil reduces internal resistance. In the field of heat resistant separators, very high heat resistance, heat sink properties, and tensile stress properties of the partially oxidized thin layer graphite piece layer in close contact with a separator made of a polymer material allows the shape to be maintained without a film rupture even at high temperatures while maintaining the shutdown function and reducing the temperature rise.

EXAMPLES

The present invention will now be specifically described in more detail with reference to examples, but these examples are not intended to limit the present invention. In the examples, parts are parts by mass unless otherwise specified. Property values in the examples were determined by the methods described below.

A. Method for Measuring Degree of Oxidation (O/C)

Samples were subjected to X-ray photoelectron spectroscopy using a PHI Quantera SXM available from Ulvac-Phi, Incorporated. Under the conditions of an excitation X-ray of monochromatic Al K$_{\alpha1,2}$ radiation (1486.6 eV), an X-ray diameter of 200 μm, and a photoelectron take-off angle of 45°, the degree of oxidation (O/C) was determined from a peak area of oxygen atoms and a peak area of carbon atoms at a wide scan.

B. Method for Measuring Surface Resistivity and Method for Peeling Tape Measurement of Surface Resistivity The measurement was made after a sample to be measured was held in an air atmosphere at a temperature of 23° C. and a humidity of 55% for one hour. Using a four-point PSP probe at an electrode spacing of 1.5 mm and an electrode radius of 0.26 mm, the measurement was made with a Loresta (registered trademark) GP (MCP-T610) available from Mitsubishi Chemical Analytech Co., Ltd. The measurement was made at ten different points of a sample before tape peeling, and eight values excluding the highest value and the lowest value was averaged to determine the surface resistivity (Ra) of the sample. For a surface that has been subjected to tape peeling, the measurement was made at selected ten different points at substantially equal intervals on the peeled surface, and a surface resistivity (Rb) was determined in the same manner as Ra.

Method for Peeling Tape

Using a CELLOTAPE (registered trademark) CT-24 available from Nichiban Co., Ltd. (tape width: 24 mm), peeling was carried out in accordance with a method described in adhesion (cross-cut method) according to JIS K 5600-5-6 under the following conditions: tape length, approximately 75 mm; length of tape application to a thin layer graphite-containing layer, approximately 50 mm; time from the start of tape application to the start of tape peeling, 3 min; tape angle in peeling (the angle between the tape still applied and the tape peeling direction), approximately 60°; time until all the tape is peeled, approximately 1 sec.

C. Method for Measuring Surface Resistivity Ra Before Tape Peeling and Coefficient of Variation CV of Layer Comprising Thin Layer Graphite Pieces A square sample 150 mm long×150 mm wide including a substrate and a layer comprising thin layer graphite pieces on the substrate was provided. The sample was dried in advance in a nitrogen atmosphere at 80° C. for at least 12 hours and then held in an air atmosphere at a temperature of 23° C. and a humidity of 55% for at least one hour, after which a measurement was made. Using an MCP-5521 automatic resistivity measurement system available from Mitsubishi Chemical Analytech Co., Ltd., surface resistivities at 100 divisions (=10×10) made by dividing the sample longitudinally and transversely both at 15-mm intervals into 10 equal parts were measured with a four-point PSP probe at an electrode spacing of 1.5 mm and an electrode radius of 0.26 mm, and from the 100 surface resistivities obtained, a standard deviation and an average value were calculated to determine the coefficient of variation CV (%).

D. Methods for Measuring Average Thickness Ta of Layer Comprising Thin Layer Graphite Pieces, Thickness Tb of Substrate, and Average Thickness T of Thin Layer Graphite Pieces Average Thickness Ta of Layer Comprising Thin Layer Graphite Pieces and Thickness Tb of Substrate A sample including a layer comprising thin layer graphite pieces and/or a substrate was prepared as described below. First, a layer comprising thin layer graphite pieces and a substrate were dried in a nitrogen atmosphere at 80° C. for at least 12 hours, and then using amorphous carbon as a surface protectant, a surface protective layer was provided on the surface of the layer comprising thin layer graphite pieces and the surface of the substrate. Next, using a Strata DB235 available from FEI at an acceleration voltage of 30 kV, the layer comprising thin layer graphite pieces was cut in the thickness direction from the surface of the layer to the substrate by a focused ion beam technique. Furthermore, using a Dual Mill 600 available from GATAN, three thin film samples were prepared from the same layer comprising thin layer graphite pieces by an ion milling technique. The thin film samples were each observed under an H-9000UHR III transmission electron microscope available from Hitachi High-Technologies Corporation at an acceleration voltage of 300 kV. The observation was carried out at 2,000,000× when the thickness was less than 50 nm, at 200,000× when 50 nm to less than 500 nm, at 20,000× when 500 nm to less than 5 µm, and at 2,000× when 5 µm or more. For the layer comprising thin layer graphite pieces, 30 different points distant from one another by at least an interval corresponding to the thickness of an electrically conductive layer were randomly selected. The average thicknesses $ta_1$, $ta_2$, and $ta_3$ of the electrically conductive layers of the samples were calculated, and $ta_1$, $ta_2$, and $ta_3$ were further averaged to determine the average thickness to of the electrode layer. Also for the substrate, 30 different points distant from one another by at least an interval corresponding to the thickness of the substrate were randomly selected. The average thicknesses $tb_1$, $tb_2$, and $tb_3$ of the substrates of the three samples were calculated, and $tb_1$, $tb_2$, and $tb_3$ were further averaged to determine the average thickness tb of the substrate. When the sample includes only the substrate, three test samples were collected from one sample, and thicknesses of 5 points at regular intervals in each test sample, 15 points in total, were measured in accordance with JIS K 6783. When the substrate thickness was less than 12 mm, the thickness was measured using a PG-02 constant-pressure thickness meter available from Teclock Corporation, and when the substrate thickness was 12 mm or more, the thickness was measured using vernier calipers. The thicknesses were averaged to determine the average thickness tb of the substrate.

Average Thickness T of Thin Layer Graphite Pieces

A sample in the form of a dispersion in a medium, such as the above-described coating agent, was embedded in an epoxy resin. In the case of powdered thin layer graphite pieces, the powder was dispersed in advance in a precursor liquid of an epoxy resin at room temperature for 5 minutes using an ultrasonic homogenizer at an output power of 100 W, and then embedded in the epoxy resin. After the sample was further dried in a nitrogen atmosphere at 80° C., thin film samples were prepared using the same apparatus under the same conditions as in the measurement of the above average thickness to and tb and further observed under a transmission electron microscope. The observation was carried out at 2,000,000× when the thickness of the thin layer graphite piece was less than 50 nm, at 200,000× when 50 nm to less than 500 nm, and at 20,000× when 500 nm to less than 5 µm. Thirty thin layer graphite pieces on one or more observation screens were randomly selected, and the maximum thickness of one domain for each piece was measured. The 30 thicknesses were averaged to determine the average thickness T of the thin layer graphite pieces.

E. Method for Measuring Average Size L of Thin Layer Graphite Pieces

A sample in the form of a dispersion of thin layer graphite pieces was applied to a clean glass substrate by spin coating, dried in a nitrogen atmosphere at 80° C., and then subjected to a measurement. Using a VK-9700 laser microscope available from Keyence Corporation, the sample was observed at a magnification that can view a field of approximately 100 µm×130 µm. Maximum particle widths of 50 thin layer graphite pieces randomly selected in the field of view were measured, and, furthermore, maximum particle widths were measured in five different fields of view distant from each other by at least 1 mm. The maximum particle widths of 250 pieces in total were averaged to determine the average size L of the thin layer graphite pieces.

F. Method for Measuring Impurities

A sample to be measured was used after being dried in a nitrogen atmosphere at 80° C. An SU8020 scanning electron microscope available from Hitachi High-Technologies Corporation including an X-Max SILICON DRIFT X-RAY DETECTOR, an energy-dispersive X-ray detector (EDX), available from Horiba, Ltd. was used. The sample was observed at an acceleration voltage of 1 kV and a magnification of 100× such that thin layer graphite occupies the whole field of view to analyze percentage atomic compositions (atomic %, hereinafter referred to as at %), proportions of atoms, in 10 different areas not overlapped with each other at all. Averages of the proportions of carbon atoms, oxygen atoms, and, if determined to be present at 0.1 at % or more, other different elements were calculated. For the elements determined to be present at 0.1 at % or more, their molecular weights or atomic weights were calculated to the first decimal place: silicon, as $SiO_2$; aluminum, as $Al_2O_3$; manganese, as $MnO_2$; sulfur, as $SO_4^{2-}$ (regarded as $SO_4$ in calculation); nitrogen, as $NO_3^-$ (regarded as $NO_3$ in calculation); other elements, as the elements (e.g., sodium, as sodium alone). For carbon (C) atoms and oxygen (O) atoms, the proportion (% by mass) of partially oxidized thin layer graphite pieces in a layer comprising the partially oxidized thin layer graphite pieces was calculated. When a dispersant is added, the amount of the dispersant was subtracted to determine the amount of carbon (C) and oxygen (O).

G. Measurement of Melting Point (Tm)

Using a differential scanning calorimeter (DSC-2) available from PerkinElmer Inc., a measurement was made with 10 mg of a sample at a heating rate of 16° C./min. The sample was once heated at a heating rate of 16° C./min to observe an endothermic peak temperature (Tm1), held for 5 minutes at a temperature higher than Tm1 by approximately 20° C., rapidly cooled to room temperature, (held at room temperature for 5 minutes inclusive of rapid cooling time), and heated again under the heating condition of 16° C./min. Tm was defined as an endothermic peak temperature observed as a crystal melting temperature during the reheating process.

H. Measurement of Thermal Diffusivity

A LaserPIT AC Method Thermal Diffusivity Measurement System available from Ulvac-Riko, Inc. was used. A sample was prepared by cutting to the size of 4 mm×40 mm and drying in a nitrogen atmosphere at 80° C., and then a measurement was made at 10 Hz in an air atmosphere at 20° C.

I. Measurement of Oxygen Permeability (Oxygen Gas Barrier Properties)

In accordance with ASTM D-3985, a measurement was made using an oxygen permeability rate test system (OX-TRAN2/21 available from MOCON) under the conditions of 23° C. and 0% RH. Oxygen permeability (cc/m$^2$·day) was defined as a plateau value in a measurement plot after 300 minutes from the start of the measurement.

J. Measurement of Hydrogen Permeability (Hydrogen Gas Barrier Properties)

In accordance with JIS K7126-1 method (differential pressure method), a measurement was made at 35° C. using a GTR-10 (Yanaco Analytical Instruments Inc). Hydrogen was used as a gas. Hydrogen permeability (cc·cm/cm$^2$·sec·cmHg) was defined as a plateau value in a measurement plot after 24 hours from the start of the measurement.

Production Example 1 (Method for Producing Physical and Chemically Thin-Layered Partially Oxidized Thin Layer Graphite Pieces)

A raw material of 10 g of a natural graphite with an average size of 80 μm available from Nippon Graphite Industries, Ltd. (type: ACB-100) was treated with a PULVERISETTE (registered trademark) P-5 planetary ball mill available from Fritsch Japan Co., Ltd. at a revolution speed of 400 rpm and a revolution/rotation ratio of 1:-2 for 6 hours to give an intermediate of physically thin-layered thin layer graphite pieces having an average size of 5.6 μm. After that, a chemical thin-layering process was performed. Specifically, to 400 parts of ice-cold 98% sulfuric acid under stirring, 15 parts of the physically thin-layered natural graphite and 5 parts of sodium nitrate with a purity of 99% or higher were added, and in addition, 10 parts of potassium permanganate with a purity of 99.3% or higher was gradually added. The resulting mixture was allowed to react at 20° C. for 4 hours. The reaction product was diluted with 400 parts of pure water under ice cooling, vigorously stirred for 15 minutes, and further diluted with 500 parts of pure water for 30 minutes under vigorous stirring. After that, 40 parts of an aqueous hydrogen peroxide solution at a concentration of 30% was added. The resulting solution was further vigorously stirred for 10 minutes, and the reaction was stopped.

The resulting mixture was centrifuged using a High Speed Refrigerated Centrifuge 778011 available from Kubota Corporation at a centrifugal force corresponding to 2,000 times gravity (2,000×G). After the centrifugation, the supernatant was removed to obtain a sample. To the sample, pure water in an amount equal to the amount of the supernatant removed was added and stirred. The resulting mixture was centrifuged again at a centrifugal force of 5,000×G for 30 minutes to obtain a solid, and then the solid was washed with pure water and centrifuged at 20,000×G. This washing with pure water and centrifugation at 20,000×G was repeated to a pH of 3 or greater. Finally, the resultant was freeze-dried to obtain chemically thin-layered partially oxidized thin layer graphite pieces A. The thin layer graphite pieces A had an average size L of 1.4 μm, an average thickness T of 3.2 nm, and a degree of oxidation (O/C) of 0.49.

Production Example 2 (Method for Producing Partially Oxidized Thin Layer Graphite Pieces by Physical Thin-Layering)

With microwaves (2.45 GHz; output power, 600 W), 2.5 g of an acid-treated graphite (type EXP-ZM) available from Nippon Graphite Industries, Ltd. was treated for 10 minutes and then treated using the same planetary ball mill under the same conditions as in Production Example 1 to give partially oxidized thin layer graphite pieces B having an average size of 6.7 μm, an average thickness of 56.1 nm, and a degree of oxidation (O/C) of 0.12.

Production Example 3

Partially oxidized thin layer graphite pieces C were obtained in the same manner as in Production Example 1 except that the natural graphite used as a raw material in Production Example 1 was thin layered only by the chemical process without the physical thin-layering process. The partially oxidized thin layer graphite pieces had an average size L of 22.6 μm, an average thickness T of 4.5 nm, and a degree of oxidation (O/C) of 0.64.

Examples 1 and 2

The partially oxidized thin layer graphite pieces A obtained in Production Example 1 in an amount of 1.0 g was mixed into 99.0 g of ion-exchanged water at room temperature of 20° C., and then the mixture was treated with an ultrasonic homogenizer (type UP400S-T) available from Hielscher at 60 W for 5 minutes to give a coating agent A containing 1% by mass of partially oxidized thin layer graphite pieces. Similarly, the partially oxidized thin layer graphite pieces B obtained in Production Example 2 in an amount of 1.0 g was mixed into N-methyl-2-pyrrolidone, and then the mixture was treated with the ultrasonic homogenizer under the same conditions to give a coating agent B containing 1% by mass of partially oxidized thin layer graphite pieces.

In producing a laminate, a Lumirror (registered trademark) polyethylene terephthalate (hereinafter referred to as PET) film (type S10; thickness, 100 μm; size, A4) available from Toray Industries, Inc. was used as a substrate made of a polymer material. As a binding agent A, 3-(2-aminoethyl)aminopropyltrimethoxysilane (type Z-6094, hereinafter also referred to as AE-APTMS) available from Dow Corning Toray Co., Ltd., which has three methoxy groups that bind to silicon atoms as first binding functional groups and one primary amine and one secondary amine as second binding functional groups, was used. The binding agent A was added to ethanol (purity: 99.5% by volume or higher) available from Wako Pure Chemical Industries, Ltd. so as to be 1% by mass and stirred to give an aqueous solution of the binding agent A. The aqueous solution of the binding agent A was then applied 200 mm wide and 200 mm long using an applicator such that the wet thickness was 1 μm. The coated substrate was then dried at 80° C. 5 minutes to load the binding agent A onto the substrate. To the binding agent, the coating agent A or the coating agent B described above was applied approximately 200 mm wide and long using an applicator such that the dry thickness would be approximately 200 nm. The substrate coated with the coating agent A was dried at atmospheric pressure at 120° C. for 5 minutes. The substrate coated with the coating agent B was dried at atmospheric pressure at 120° C. for 15 minutes and then dried under vacuum at 120° C. for 1 hour. A layer A or a layer B containing partially oxidized thin layer graphite pieces in an amount of 100% by mass was formed. After that, the laminates each including the layer A or layer B containing thin layer graphite pieces were reduced by immersion in a 20% by mass aqueous solution of hydrazine monohydrate for 15 minutes in a draft chamber. The edge, where the partially reduced thin layer graphite piece layer was insufficiently formed, was cut off to obtain a laminate A (Example 1) and a laminate B (Example 2) in the form of a square sheet 150 mm long×150 mm wide. The laminate A and the laminate B were both laminates in the form of a sheet having an extremely smooth surface with a metallic luster. In the partially reduced thin layer graphite piece layers, elements other than carbon and oxygen atoms were below the lower limit of measurement and not observed, except that silicon (Si) was observed at 0.1 at %.

It can be seen from Table 1 that the laminate A and the laminate B each have a good surface resistivity Ra, surface resistivity after tape peeling Rb, and coefficient of variation CV of surface resistivity Ra, thus having high electrical conductivity. Presumably, methoxysilyl groups (first binding functional groups) of AE-APTMS and primary amino groups and secondary amino groups (second binding functional groups) formed chemical bonds (the first binding functional groups formed covalent bonds: silyl ether bonds) between the substrate and the thin layer graphite piece layer, and the second binding functional groups (primary amino groups and secondary amino groups) and carboxyl groups or hydroxyl groups of the partially oxidized thin layer graphite pieces were bound to each other via ionic bonds or hydrogen bonds. It has been suggested that the laminate A and the laminate B undergoes little change in electrical conductive properties even if degradation of surface quality due to physical contact has finally occurred and can be used as excellent electrical conductors.

Comparative Example 1 and Example 3

A laminate C (Comparative Example 1) and a laminate D (Example 3) in the form of a sheet were produced using the same raw materials and the same procedure under the same conditions as in Example 1 except that the binding agent A was not used (Comparative Example 1), or the binding agent A was not used and the substrate was subjected to UV ozonation for 10 minutes (Example 3). The laminate C and the laminate D both had a good surface resistivity Ra.

The laminate C, however, had a large coefficient of variation CV of surface resistivity Ra, as shown in Table 1. In addition, the whole partially reduced thin layer graphite piece layer (electrode layer) was peeled off the substrate as a result of tape peeling. Thus, surface resistivity Rb after tape peeling was over the upper limit of measurement of the apparatus and unmeasurable, and Rr was incalculable. In Comparative Example 1, no chemical bond was formed between the substrate and the thin layer graphite pieces because pretreatment of the substrate and a binding agent were not employed. As a result, the electrode layer made of the thin layer graphite piece layer was not able to tightly adhere to the substrate, resulting in uneven electrical conductivity. Thus, degradation in physical properties due to physical contact could not be reduced.

The laminate D of Example 3 had a coefficient of variation CV of surface resistivity Ra larger than that of Example 1, but within the acceptable range, and a surface resistivity Rb after tape peeling and a calculated Rr larger than those of Example 1, but within the acceptable range, as shown in Table 1. In the laminate D, chemical bonds were formed between hydroxyl groups of the substrate formed by UV ozonation and carboxyl groups of the thin layer graphite piece layer, thus successfully reducing the degradation in physical properties due to physical contact.

Example 4 and Comparative Example 2

Similarly to Comparative Example 1, a laminate E (Example 4) and a laminate F (Comparative Example 2) in the form of a sheet were produced using the same raw materials and the same procedure under the same conditions as in Example 1 except that the binding agent A was replaced respectively with 3-glycidoxypropyltrimethoxysilane available from Dow Corning Toray Co., Ltd. (type Z-6040, hereinafter also referred to as GPTMS: a binding agent B, Example 4) and phenyltrimethoxysilane available from Dow Corning Toray Co., Ltd. (type Z-6124, hereinafter also referred to as PhTMS: a binding agent C, Comparative Example 2).

The laminate E had a metallic luster and, as shown in Table 1, had a good surface resistivity Ra and a good coefficient of variation CV of surface resistivity Ra, although the value was larger than that of Example 1. Furthermore, the laminate E had a good surface resistivity Rb after tape peeling and a good calculated Rr, although the values were larger than those of Example 1. This is probably because, in the laminate E, silyl ether bonds were formed between the substrate and the binding agent B, and chemical bonds were formed between glycide groups of the binding agent B and the thin layer graphite piece layer, thus successfully reducing the degradation in physical properties due to physical contact.

The laminate F had a metallic luster and, as shown in Table 1, had a good surface resistivity Ra but a large coefficient of variation CV of surface resistivity Ra approximately three times that of Example 1, showing variation in electrical conductivity on the surface. Furthermore, the laminate F had a surface resistivity Rb after tape peeling and a calculated Rr much larger than those of Example 1, showing that the degradation in physical properties due to physical contact was less effectively reduced. Presumably, phenyl groups, the second binding functional groups of the binding agent, although having a modest affinity to the thin layer graphite piece layer due to hydrophobic interaction, formed no chemical bonds, thus not leading to tight adhesion of the electrode layer made of partially oxidized thin layer graphite pieces to the substrate. Thus, the electrical conductivity was uneven, and the degradation in physical properties due to physical contact could not be reduced.

Examples 5 and 6

A laminate G (Example 5) and a laminate H (Example 6) in the form of a sheet were produced using the same raw materials and the same procedure under the same conditions as in Example 1 except that the partially oxidized thin layer graphite pieces A obtained in Production Example 1 was applied and loaded such that the dry thickness would be approximately 500 nm (Example 5) or approximately 20 nm (Example 6). The laminate G had a metallic luster and, as shown in Table 1, had an excellent surface resistivity Ra, a small surface resistivity after tape peeling Rb, a small Rr, and a coefficient of variation CV of surface resistivity Ra, thus having excellent electrical conductivity. The laminate H had a metallic luster and, as shown in Table 2, had good electrical conductivity although the surface resistivity was larger than that of Example 1 due to its very thin coating, and the electrode layer was very thin and smooth. The laminate G and the laminate H were both found to be usable as an excellent electrical conductor.

The thermal diffusivity of the laminate G obtained in Example 5 was measured to be a preferred value of $5.2 \times 10^{-4}$ $m^2/s$.

The oxygen permeabilities of the laminate H obtained in Example 6 and, for comparison, of the above-described PET film including a substrate alone on which no thin layer graphite was loaded were measured. The PET film alone had oxygen barrier properties of 15.8 $cc/m^2 \cdot day$, and the laminate H had an excellent oxygen barrier properties of $1.43 \times 10^{-2}$ $cc/m^2 \cdot day$ Example 7

A laminate I in the form of a sheet was produced using the same raw materials and the same procedure under the same conditions as in Example 1 except that the binding agent A was replaced with a binding agent D 3-aminopropyltrimethoxysilane available from Dow Corning Toray Co., Ltd. (type Z-6610, hereinafter also referred to as APTMS), and the partially oxidized thin layer graphite pieces C prepared in Production Example 3 were used as partially oxidized thin layer graphite pieces. The laminate I had a metallic luster and, as shown in Table 2, had an excellent surface resistivity Ra. The value of coefficient of variation CV of surface resistivity Ra was small, as with Example 1, and the values of surface resistivity Rb after tape peeling and calculated Rr were good, as with Example 1. In the laminate I, chemical bonds were formed between the substrate and the thin layer graphite pieces via the binding agent D (silyl ether bonds between the substrate and the first binding functional groups of the binding agent D, and ionic bonds and hydrogen bonds between the second binding functional groups (primary amino groups and secondary amino groups) of the binding agent D and carboxyl groups and hydroxyl groups of the partially oxidized thin layer graphite pieces), thus reducing the degradation in physical properties due to physical contact.

Examples 8 and 9

In Example 8, an A4-sized Kapton (registered trademark) polyimide film (Du Pont-Toray Co., Ltd., type 500H; average thickness, 125 μm) surface treated by UV ozonation for 30 seconds was used as a substrate in place of the PET film in Example 1. In Example 9, an A4-sized Rayfan (registered trademark) NO polyamide 6 film (Toray Advanced Film Co., Ltd., type 1401; average thickness, 30 μm) surface treated by UV ozonation for 30 seconds was used as a substrate. A laminate J (Example 8) and a laminate K (Example 9) in the form of a sheet were produced using the same raw materials and the same procedure under the same conditions as in Example 1 except that the substrate was changed and the binding agent D used in Example 7 was used. The laminate J and the laminate K both had a metallic luster and, as shown in Table 2, had an excellent surface resistivity Ra. The values of coefficient of variation CV of surface resistivity Ra were small, as with Example 1, and the values of surface resistivity Rb after tape peeling and calculated Rr were good, as with Example 1. In the laminate J and the laminate K, chemical bonds were formed between hydroxyl groups or carboxyl groups of the substrate formed by UV ozonation and the thin layer graphite pieces (ionic bonds or hydrogen bonds between hydroxyl groups or carboxyl groups presumably formed on the substrate by ozonation and hydroxyl groups and carboxyl groups of the partially oxidized thin layer graphite pieces), thus successfully reducing the degradation in physical properties due to physical contact.

The oxygen permeabilities of the laminate K obtained in Example 9 and, for comparison, of the above-described polyamide 6 film substrate alone on which no thin layer graphite was loaded were measured. The polyamide 6 film alone had oxygen gas barrier properties of 21.3 cc/m$^2$·day, and the laminate K had excellent oxygen gas barrier properties of $1.76 \times 10^{-2}$ cc/m$^2$·day. Furthermore, the hydrogen permeabilities of the laminate K obtained in Example 9 and, for comparison, of the above-described polyamide 6 film substrate alone on which no thin layer graphite was loaded were measured. The polyamide 6 film alone had hydrogen barrier properties of $7.23 \times 10^{-11}$ cc·cm/cm$^2$·sec·cmHg, and the laminate K had excellent hydrogen barrier properties of $3.67 \times 10^{-13}$ cc·cm/cm$^2$·sec·cmHg.

Comparative Example 3

A laminate L in the form of a sheet was produced using the same raw materials and the same procedure under the same conditions as in Example 1 except that the thin layer graphite A was replaced with a DENKA BLACK (registered trademark) acetylene black powder (average primary particle size: 35 nm) available from Denki Kagaku Kogyo Kabushiki Kaisha. No binder was used in the coating agent. The laminate L did not have a metallic luster and remained black after the reduction treatment, and no phenomenon that supported the formation of chemical bonds with the binding agent, such as delamination of the acetylene black layer, did not occur during the reduction. As shown in Table 2, the values of surface resistivity Ra and coefficient of variation CV of surface resistivity Ra were both larger than those of Example 1. Furthermore, the layer of acetylene black peeled off the substrate as a result of tape peeling. Surface resistivity Rb after tape peeling was over the upper limit of measurement of the apparatus and could not be measured by the method in Section B, and Rr was incalculable. Presumably, the binding agent A and acetylene black formed almost no chemical bond. Moreover, the layer made of acetylene black practically could not adhere to the substrate. Furthermore, since no binder was used because of the weak interaction of the acetylene black itself, it was difficult to stably form a layer for an electrode. Thus, electrical conductivity was uneven, and the degradation in physical properties due to physical contact could not be reduced at all.

Example 10

A laminate M in the form of a sheet was produced using the same raw materials and the same procedure under the same conditions as in Example 1 except that a Lumirror (registered trademark) PET film available from Toray Industries, Inc. (type E28G; thickness, 100 μm; size, A4) was used as a substrate made of a polymer material, and the binding agent A was not used. To the E28G PET film, an ester polymer (binding agent E) that readily exhibits adhesion upon heating was bonded as a binding agent. The laminate M had a metallic luster and, as shown in Table 2, had an excellent surface resistivity Ra. The value of coefficient of variation CV of surface resistivity Ra was small, as with Example 1, and the values of surface resistivity Rb after tape peeling and calculated Rr were good, as with Example 1. In the laminate M, chemical bonds were formed between hydroxyl groups and ester groups of the substrate and the first binding functional groups of the binding agent E and between hydroxyl groups and ester bonds, the second binding functional groups, of the binding agent E and carboxyl groups and hydroxyl groups of the thin layer graphite pieces, thus successfully reducing the degradation in physical properties due to physical contact. One possible reason is that the PET film and the binding agent E, or the binding agent E and the thin layer graphite pieces, were similar in chemical structure, and in part, hydrogen bonds and ionic bonds derived from terminal hydroxyl groups present in large numbers in the ester were formed, or ester reaction and/or transesterification reaction were effected to form a new chemical bond (covalent bond).

The hydrogen permeabilities of the laminate M and, for comparison, of the E28G PET film used as a substrate alone on which no thin layer graphite was loaded were measured. The E28G PET film alone had hydrogen barrier properties of $1.09 \times 10^{-10}$ cc·cm/cm$^2$·sec·cmHg, and the laminate M had excellent hydrogen barrier properties (hydrogen blocking properties) of $5.82 \times 10^{-13}$ cc·cm/cm$^2$·sec·cmHg.

Example 11

A laminate N in the form of a sheet was produced using the same raw materials and the same procedure under the same conditions as in Example 1 except that a Lumirror (registered trademark) PET film available from Toray Industries, Inc. (type E28G; thickness, 100 μm; size, A4) was used as a substrate made of a polymer material; the binding agent A was not used; the coating agent A was also not used; and a coating agent C described below was prepared and used in place. On the E28G PET film, the binding agent E was separately loaded in advance.

The coating agent C was prepared as described below. First, 1.6 g of the partially oxidized thin layer graphite pieces A obtained in Production Example 1 was mixed into 48.4 g of ion-exchanged water at 20° C. Next, the mixture was treated using an ultrasonic homogenizer (type UP400S-T) available from Hielscher under the condition of 100 W, while in a draft chamber, 50.0 g of a 20% by mass aqueous solution of hydrazine monohydrate was added to effect a reduction reaction for 60 minutes. The reaction solution was filtered to give 24 g of a water cake at a concentration of 4.0% by mass, after which 72 g of NMP was added thereto, and the mixture was subjected to a dispersion treatment again using the ultrasonic homogenizer at 100 W for 15 minutes to give reduced partially oxidized thin layer graphite pieces. Following the dispersion treatment, the resultant was filtered to give 24 g of a water/NMP cake at a concentration of 4.0% by mass. Finally, NMP was added to the cake, and then the resultant was subjected to a dispersion treatment using the ultrasonic homogenizer at 100 W for 15 minutes to give the coating agent C containing 1% by mass of the reduced partially oxidized thin layer graphite pieces A.

The laminate N had a metallic luster and, as shown in Table 2, had an excellent surface resistivity Ra. The value of coefficient of variation CV of surface resistivity Ra was small, as with Example 1, and the values of surface resistivity Rb after tape peeling and calculated Rr were good, as with Example 1. In the laminate N, as with Example 10, chemical bonds were formed between the substrate and the thin layer graphite pieces via the binding agent E (ester bonds and/or hydrogen bonds between the substrate and the first binding functional groups of the binding agent E (hydroxyl groups and ester groups), and ester bonds and hydrogen bonds between the second binding functional groups (hydroxyl groups and ester groups) of the binding agent E and carboxyl groups and hydroxyl groups of the partially oxidized thin layer graphite pieces), thus successfully reducing the degradation in physical properties due to physical contact.

TABLE 1

| | Unit | Example 1 | Example 2 | Comparative Example 1 | Example 3 | Example 4 | Comparative Example 2 | Example 5 |
|---|---|---|---|---|---|---|---|---|
| Average Thickness T of Thin Layer Graphite Pieces in Coating Agent | nm | 3.2 | 56.1 | 3.2 | 3.2 | 3.2 | 3.2 | 3.2 |
| Average Size L of Thin Layer Graphite Pieces in Coating Agent | μm | 1.4 | 6.7 | 1.4 | 1.4 | 1.4 | 1.4 | 1.4 |
| Degree of Oxidation [O/C] of Partially Oxidized Thin Layer Graphite Pieces in Coating Agent | — | 0.49 | 0.12 | 0.49 | 0.49 | 0.49 | 0.49 | 0.49 |
| Degree of Oxidation [O/C] of Partially Reduced Thin Layer Graphite Pieces After Reduction Treatment | — | 0.14 | 0.09 | 0.14 | 0.14 | 0.14 | 0.14 | 0.14 |
| Material of Substrate | — | PET | PET | PET | PET | PET | PET | PET |
| Average Thickness tb of Substrate | μm | 100 | 100 | 100 | 100 | 100 | 100 | 100 |
| Binding Agent | — | AE-APTMS | AE-APTMS | — | — | GPTMS | PhTMS | AE-APTMS |
| First Binding Functional Group, Type of Chemical Bond | — | Methoxysilane, Covalent bond | Methoxysilane, Covalent bond | — | Hydroxyl and carboxyl, Hydrogen bond (*2) | Methoxysilane, Covalent bond | Methoxysilane, Covalent bond | Methoxysilane, Covalent bond |
| Second Binding Functional Group, Type of Chemical Bond | — | Primary amine and secondary amine, Ionic bond | Primary amine and secondary amine, Ionic bond | — | — | Glycidyl ether, Covalent bond | Phenyl, Hydrophobic interaction | Primary amine and secondary amine, Ionic bond |
| Ra | Ω/sq | 92 | 83 | 148 | 119 | 99 | 136 | 37 |
| Coefficient of Variation CV of Ra | % | 2.1 | 1.9 | 10.5 | 4.9 | 3.8 | 6.3 | 2.6 |
| Rb | Ω/sq | 99 | 183 | Unmeasurable | $1.09 \times 10^4$ | 130 | $3.52 \times 10^5$ | 39 |
| Rr | — | 1.08 | 2.21 | Incalculable | 92 | 1.31 | $2.59 \times 10^3$ | 1.06 |
| Average Thickness ta of Partially Oxidized (Partially Reduced) Thin Layer Graphite Piece Layer | nm | 203 | 201 | 210 | 202 | 205 | 208 | 496 |
| Form of Laminate | — | Sheet | Sheet | Sheet | Sheet | Sheet | Sheet | Sheet |

TABLE 2

| | Unit | Example 6 | Example 7 | Comparative Example 1 | Example 9 | Comparative Example 3 | Comparative Example 2 | Example 11 |
|---|---|---|---|---|---|---|---|---|
| Average Thickness T of Thin Layer Graphite Pieces in Coating Agent | nm | 3.2 | 4.5 | 3.2 | 3.2 | 35 (*1) | 3.2 | 11 |
| Average Size L of Thin Layer Graphite Pieces in Coating Agent | μm | 1.4 | 22.6 | 1.4 | 1.4 | 35 (*1) | 1.4 | 1.1 |
| Degree of Oxidation [O/C] of Partially Oxidized Thin Layer Graphite Pieces in Coating Agent | — | 0.49 | 0.64 | 0.49 | 0.49 | 0.01 | 0.49 | 0.2 |
| Degree of Oxidation [O/C] of Partially Reduced Thin Layer Graphite Pieces Alter Reduction Treatment | — | 0.14 | 0.15 | 0.14 | 0.14 | 0.01 | 0.14 | 0.11 |
| Material of Substrate | — | PET | PET | PI | Polyamide 6 | PET | PET | PET |
| Average Thickness tb of Substrate | μm | 100 | 100 | 125 | 30 | 100 | 100 | 100 |
| Binding Agent | — | AE-APTMS | APTMS | APTMS | APTMS | AE-APTMS | Ester polymer | Ester polymer |
| First Binding Functional Group, | — | Methoxysilane, | Methoxysilane, | Methoxysilane, | Methoxysilane, | Methoxysilane, | Hydroxyl, | Hydroxyl, |
| Type of Chemical Bond | | Covalent bond | Covalent bond | Covalent bond | Covalent bond | Covalent bond | Hydrogen/ covalent bond | Hydrogen/ covalent bond |
| Second Binding Functional Group, | — | Primary amine and secondary amine, | Primary amine, | Primary amine, | Primary amine, | Primary amine and secondary amine, | Hydroxyl, | Hydroxyl, |
| Type of Chemical Bond | | Ionic bond | Ionic bond | Ionic bond | Ionic bond | Ionic bond | Hydrogen/ ionic bond | Hydrogen/ ionic bond |
| Ra | Ω/sq | 913 | 86 | 101 | 89 | 682 | 86 | 125 |
| Coefficient of Variation CV of Ra | % | 2.4 | 1.9 | 3 | 1.9 | 20.1 | 1.9 | 3.8 |
| Rb | Ω/sq | 1080 | 90 | 120 | 97 | Unmeasurable | 97 | 159 |
| Rr | — | 1.18 | 1.05 | 1.19 | 1.09 | Incalculable | 1.13 | 1.27 |
| Average Thickness ta of Partially Oxidized (Partially Reduced) Thin Layer Graphite Piece Layer | nm | 20 | 201 | 204 | 199 | 138 | 202 | 198 |
| Form of Laminate | — | Sheet | Sheet | Sheet | Sheet | Sheet | Sheet | Sheet |

Notes in Table 1 and Table 2
Description of Abbreviations
PET: polyethylene terephthalate
AE-APTMS: 3-(2-aminoethyl)aminopropyltrimethoxysilane
GPTMS: 3-glycidoxypropyltrimethoxysilane
PhTMS: phenyltrimethoxysilane
PI: polyimide
APTMS: 3-aminopropyltrimethoxysilane
1: Because of particulates, the thickness and the size are the same.
2: Direct chemical bond between substrate and partially oxidized thin layer graphite pieces

INDUSTRIAL APPLICABILITY

The laminate of the present invention, when electrical conductivity, one of its excellent properties, is utilized, can be used, for example, as an electrode material in an element of various electrical equipment, particularly, as an electrode material that sends and receives electrical signals in a chemical sensor. In particular, the laminate can be used as an electrode that has a shape of a card or a chip and connects a sample contact portion to a transducer in portable sensors, such as ion sensors, bioaffinity sensors, and gas sensors. Furthermore, when thermal conductivity, one of the excellent properties of the laminate, is utilized, the laminate can be used in household electronic appliances, particularly, information terminal devices that place importance on portability, such as tablet computers, cellular phones, and smartphones. Furthermore, when gas barrier properties, one of the excellent properties of the laminate, is utilized, the laminate can be used as a gas barrier material having so excellent gas blocking properties that block water vapor, oxygen, and other gases particularly at a display unit where outside air should be blocked in an information terminal device, and can be used as a gas barrier material that blocks natural gas and hydrogen gas from diffusing out through a tank inner layer of a barrier resin layer in a high-pressure gas tank, particularly, an LNG tank for natural gas vehicles and a hydrogen gas tank for fuel cell vehicles, which are expected to increasingly come into the market in the future. Furthermore, the laminate can be provided as a gas barrier material that blocks gas permeation also in hoses to supply gases to such gas tanks, various flexible pipes attached to hydrogen stations and hydrogen generators, and other gas supply equipment. In addition, the laminate can be widely used as a high-functional material having these plural high functions.

DESCRIPTION OF SYMBOLS

1: Substrate
2: Binding agent
3: Partially oxidized thin layer graphite piece layer
4: Laminate

The invention claimed is:

1. A laminate comprising at least:
   a substrate made of a polymer material; and
   a partially oxidized thin layer graphite piece layer comprising partially oxidized thin layer graphite pieces and having an average thickness to of 3.0 nm to 10,000 nm,
   the layer being formed on the substrate and bonded to the substrate via a chemical bond;
   wherein the chemical bond is formed by a binding agent having a first binding functional group forming a first chemical bond with the substrate and a second binding functional group forming a second chemical bond with partially oxidized thin layer graphite pieces;
   wherein the first binding functional group is selected from the groups of a hydroxyl group, a carboxyl group, an alkoxysilyl group and a thiol group, and the second functional group is selected from the groups of a primary amino group, a secondary amino group, a tertiary amino group, and a quaternary ammonium group.

2. The laminate according to claim 1, wherein the partially oxidized thin layer graphite pieces have a degree of oxidation (O/C) of 0.07 to 0.85.

3. The laminate according to claim 1, wherein the partially oxidized thin layer graphite piece layer is substantially free of a binder.

4. The laminate according to claim 1, wherein the chemical bond is selected from the group consisting of an ionic bond, a hydrogen bond, and a covalent bond.

5. The laminate according to claim 1, wherein the binding agent is a polymer binding agent.

6. The laminate according to claim 1, wherein the partially oxidized thin layer graphite piece layer has a surface resistivity Ra with a coefficient of variation CV of 10% or less.

7. The laminate according to claim 1, wherein the partially oxidized thin layer graphite piece layer has an insulating portion having a degree of oxidation (O/C) of at least 0.15 and an electrically conductive portion having a degree of oxidation (O/C) of less than 0.15.

8. An electrode material comprising the laminate according to claim 1.

9. A heat radiation material comprising the laminate according to claim 1.

10. A gas barrier material comprising the laminate according to claim 1.

11. A gas tank comprising the gas barrier material according to claim 10.

12. A method for producing the laminate of claim 1, the method comprising in sequence:
    loading a binding agent onto a substrate made of a polymer material, the binding agent having a first binding functional group capable of forming a chemical bond with the substrate and a second binding functional group capable of forming a chemical bond with partially oxidized thin layer graphite pieces, thereby chemically binding the substrate to the first binding functional group;
    loading a coating agent comprising partially oxidized thin layer graphite pieces onto the binding agent by application, thereby chemically binding the second binding functional group to the partially oxidized thin layer graphite pieces; and
    reducing at least some of the partially oxidized thin layer graphite pieces in a liquid.

* * * * *